(12) United States Patent
Chong et al.

(10) Patent No.: US 8,183,048 B2
(45) Date of Patent: May 22, 2012

(54) ASSAY FOR SCREENING/RANKING ANTIOXIDANTS BASED ON THEIR EFFECTS ON MEMBRANE STEROL LATERAL ORGANIZATION

(75) Inventors: Parkson Lee-Gau Chong, Cherry Hill, NJ (US); Michelle Olsher, Philadelphia, PA (US); Su-In Yoon, Singapore (SG)

(73) Assignee: Temple University- Of the Commonwealth System of Higher Education, Philadelphia, PA (US)

( * ) Notice: Subject to any disclaimer, the term of this patent is extended or adjusted under 35 U.S.C. 154(b) by 228 days.

(21) Appl. No.: 12/668,330

(22) PCT Filed: Jul. 25, 2008

(86) PCT No.: PCT/US2008/071107
§ 371 (c)(1),
(2), (4) Date: Jan. 8, 2010

(87) PCT Pub. No.: WO2009/015307
PCT Pub. Date: Jan. 29, 2009

(65) Prior Publication Data
US 2010/0291687 A1    Nov. 18, 2010

Related U.S. Application Data

(60) Provisional application No. 60/951,848, filed on Jul. 25, 2007.

(51) Int. Cl.
*G01N 33/92* (2006.01)
(52) U.S. Cl. ............... 436/71; 436/13; 436/93; 436/164; 436/172; 436/904; 422/430; 422/82.08
(58) Field of Classification Search .................... 436/13, 436/71, 93, 164, 172, 904; 422/82.05, 82.08, 422/430; 424/450
See application file for complete search history.

(56) References Cited

U.S. PATENT DOCUMENTS

| | | | |
|---|---|---|---|
| 6,841,539 | B1 | 1/2005 | Mehta et al. |
| 2004/0259187 | A1 | 12/2004 | Aldini et al. |
| 2008/0177059 | A1* | 7/2008 | Bittman et al. ............ 540/4 |

OTHER PUBLICATIONS

Olsher et al. Abstract from Biophysical Journal, vol. 86, No. 1, Jan. 2004, pp. 196a.*
Olsher et al. Biochemistry, vol. 44, Jan. 22, 2005, pp. 2080-2087.*
Sargis et al. Free Radical Biology & Medicine, vol. 40, 2006, pp. 2092-2102.*
Olsher et al. Analytical Biochemistry, vol. 382, Jul. 29, 2008, pp. 1-8.*
Cheng et al., "Fluorescence Studies of Dehydroergosterol in Phosphatidylethanolamine/Phosphatidylcholine Bilayers", Biophysical Journal, vol. 77 (1999), pp. 3108-3119.
Wharton et al., "Use of fluorescent probes in the study of phospholipid-sterol bilayers", Biochem. J., vol. 191 (1980), pp. 785-790.
International Search Report for PCT/US08/71107, May 26, 2009.

* cited by examiner

*Primary Examiner* — Maureen Wallenhorst
(74) *Attorney, Agent, or Firm* — Caesar, Rivise, Bernstein, Cohen & Pokotilow, Ltd.

(57) ABSTRACT

A method of screening an antioxidant for potency and/or toxicity in vitro, the method includes contacting the antioxidant with a model system containing a sterol superlattice formation capable of generating a detectable signal, wherein the detectable signal changes in a parameter representative of an integrity of the sterol superlattice formation; and detecting and/or measuring disruption of the sterol superlattice formation, wherein the disruption is caused by the insertion of the antioxidant into membranes and thereby screening the antioxidant for potency and/or toxicity.

16 Claims, 9 Drawing Sheets

Flow Chart and Schematic Illustration of our Design Concept

ASSAY FOR SCREENING/RANKING ANTIOXIDANTS BASED ON THEIR EFFECTS ON MEMBRANE STEROL LATERAL ORGANIZATION

BACKGROUND OF THE INVENTION

1. Field of Invention

This invention relates to a method for a quantitative screening of antioxidants for potency and toxicity based on their effect on sterol superlattice formation.

2. Description of Related Art

Reactive oxygen species (ROS) are thought to play a major role in the initiation of inflammation and pathophysiological changes associated with conditions such as Alzheimer's Disease, cancer and coronary heart disease (1, 2, 3, 4, 5, 6, 7). Oxidative damage of membrane lipids by ROS should in theory be reduced or prevented by the action of lipid-soluble antioxidants. Vitamin E, beta-carotene, and ascorbyl palmitate (lipid-soluble form of vitamin C) have all been candidates in the search for a membrane-soluble supplement that would counteract the damage caused by free radicals. Recently, there has been so much conflicting information about these antioxidants that supplementation is not recommended.

Lipophilic antioxidants (e.g., α-tocopherol and ascorbyl palmitate), have received conflicting reviews regarding their value as preventative or curative agents. Initially, lipophilic antioxidants were thought to confer cardioprotective or other types of benefits; however, more recent studies have shown that these substances can be ineffective or even harmful.

Alpha-tocopherol (vitamin E) was believed to be cardioprotective (8, 9) and to be associated with a reduction of risk in prostate, breast and other types of cancers (10, 11, 12, 13), as well as with a decrease in ROS-induced damage (14). Recently, however, a number of clinical trials have dampened the initial enthusiasm about vitamin E therapy. In a meta-analysis by Miller et al., high doses of vitamin E were associated with an increase in "all-cause mortality" (15). The Women's Angiographic Vitamin and Estrogen (WAVE) Trial demonstrated no improvement in coronary angiographic findings in women on hormone replacement therapy and taking vitamins C and E when compared with placebo (16). In general, nearly all of the most recent data do not support the use of vitamin E in cardiovascular disease and cancer prevention (17).

Beta-carotene was also thought to be cardioprotective and to reduce atherosclerotic progression (18, 19). As in the case of vitamin E, beta-carotene supplementation was recommended in the prevention and treatment of cardiovascular disease, cancer and smoking-related conditions (20, 21). Again, conflicting information from more recent studies show an increased risk with beta-carotene therapy, especially in smokers (22). Several large prevention trials involving carotenoids produced disappointing and inconclusive results; the use of beta-carotene is not recommended (23).

Ascorbyl palmitate is a lipid-soluble ester of ascorbic acid (vitamin C) and palmitic acid. This compound disperses in biomembranes, but still retains the antioxidant properties of ascorbic acid (24). Although ascorbyl palmitate is a synthetic compound, it has been proposed as a mechanism to transport ascorbic acid into neural and other tissues (25, 26), and is used in many topical formulations. As with the other previously mentioned lipophilic antioxidants, different studies show ascorbyl palmitate to either protect against free radical damage (27, 28, 29, 30) or to induce further free radical damage (31, 32, 33).

It is unclear, why these lipid-soluble antioxidants may cause damage in some cases but not in others. Some hypotheses have been put forward, but there is no consensus. According to Heinecke (34), a major problem is that there is surprisingly little evidence that compounds which display antioxidant activities in vitro actually inhibit oxidative reactions in vivo. The problem is that reactive intermediates produced by the oxidation process are short-lived and difficult to monitor and quantify. For example, it would be necessary to identify a reliable marker of in vivo lipid peroxidation in order to monitor the effects of vitamin E on lipid oxidation (34). Such biochemical markers may not be readily apparent in an in vitro study. Some of the deleterious effects seen in studies of beta-carotene could have to do with the fact that the formation of beta-carotene degradation products is directly proportional to the degree of oxidative stress. These products are toxic to cells, and contribute to the increase in carcinogenic effects that are seen in smokers using beta-carotene (35). In a similar hypothesis, Meves et al. propose that the lipid component of ascorbyl palmitate probably contributes to the generation of toxic oxidized lipid metabolites (31). Finally, Pinnell discusses the possible toxicity of ascorbyl palmitate. He hypothesizes that when the ascorbyl free radical is produced in the aqueous phase (from ascorbic acid), it is relatively weak and readily reduced. However, when the free radical is produced in the membrane environment (from ascorbyl palmitate), it may cause irreversible damage before it is reduced (33). Clearly, the status of lipophilic antioxidants is in question. Until conclusive evidence exists that these compounds confer a significant benefit, their use is not recommended. The widespread disagreement over the use of lipophilic antioxidants also demonstrates the need for more fundamental studies of antioxidant-membrane interactions.

Since these antioxidants reside in the membrane, an understanding of membrane structure should provide important information about the action of a lipid-soluble antioxidant.

The presence of a lag phase by antioxidants in AAPH-induced oxidation is known in the literature (36-42). However, there are no studies that link sterol lateral organization with the potency and adverse effect of lipid-soluble antioxidants. Known screening assays have ranked antioxidants either on the basis of the antioxidant-induced lag phase, or by the ability to reduce preformed radicals. None of these previous studies used detectable sterols. They examined non-sterol probe oxidation in buffer and serum samples. Despite current developments, there is a need for a method of a quantitative screening of antioxidants for potency and toxicity.

All references cited herein are incorporated herein by reference in their entireties.

BRIEF SUMMARY OF THE INVENTION

In one aspect, the invention is a method of screening an antioxidant for potency and/or toxicity in vitro, the method includes contacting the antioxidant with a model system comprising a sterol superlattice formation capable of generating a detectable signal, wherein the detectable signal changes in a parameter representative of an integrity of the sterol superlattice formation; and detecting and/or measuring disruption of the sterol superlattice formation, wherein the disruption is caused by oxidation of sterol upon contacting sterol with a prooxidant and the antioxidant and thereby screening the antioxidant for potency and/or toxicity.

In another aspect, the invention is a method of identifying an antioxidant activity of a compound, the method comprising detecting and/or measuring disruption of a sterol superlattice formation, wherein the disruption is caused by oxidation of sterol upon contacting sterol with a prooxidant and the compound.

In another aspect, the invention is a kit for performing an assay for screening and/or ranking antioxidants for strength and toxicity in vitro, the kit comprising: (a) a set of calibrating liposomes where each liposome comprises a fluorescent sterol probe and a phospholipid, wherein a mole fraction of the fluorescent sterol probe is varied from 18 mol % to 52 mole %; (b) an antioxidant; and (c) a prooxidant.

BRIEF DESCRIPTION OF SEVERAL VIEWS OF THE DRAWINGS

FIG. 1 illustrates how after the addition of a prooxidant at point A, the fluorescence intensity sharply drops. At point B, an antioxidant is added to one of the samples, leading to the observation of a lag phase before the fluorescence intensity drops at point C. The sudden drop in intensity between point A and B is due to energy transfer between DHE and 2,2'-azobis(2-amidinopropane) dihydrochloride (AAPH).

DETAILED DESCRIPTION OF PREFERRED EMBODIMENTS OF THE INVENTION

This invention is a novel spectroscopic method, which uses sterol superlattice formation as a tool to quantitatively assess the potentially harmful effects of antioxidants and to quantitatively access potency of antioxidants.

Inventors have discovered that conditions under which lipophilic antioxidants may be detrimental to sterol superlattice formation can be studied in a model system. Advantageously, inventors linked sterol lateral organization with the potency and adverse effect of antioxidants, preferably lipid-soluble antioxidants. In order to demonstrate how changes in membrane lateral organization affect the potency of an antioxidant or vise versa, it is necessary to prepare vesicle samples that differ in the mole fraction of sterol by only a small increment (e.g., ~0.3 mol %) and spread over a wide sterol mole fraction region such that each sample differs slightly only in the mole fraction of sterol (absolute number of sterol molecules remains constant).

In this invention, the effects of lipophilic antioxidants were examined from a membrane biophysics point of view. Inventors focused on physical principles of membranes that can affect the potency of antioxidants, and used this information to evaluate the adverse effects seen in some large-scale clinical trials. There is considerable evidence suggesting that sterol molecules form regularly distributed superlattices within the plane of the membrane (45-50). The sterol superlattice theory describes how the lateral organization of membrane sterol can affect many membrane-associated properties, such as the activity of some surface-acting enzymes and membrane-bound proteins and the partitioning of nystatin into the bilayer (51-56). Inventors have now discovered that the lateral organization of membrane sterol can serve as an indicator of the potential toxicity of a lipid-soluble antioxidant.

Figure 9:
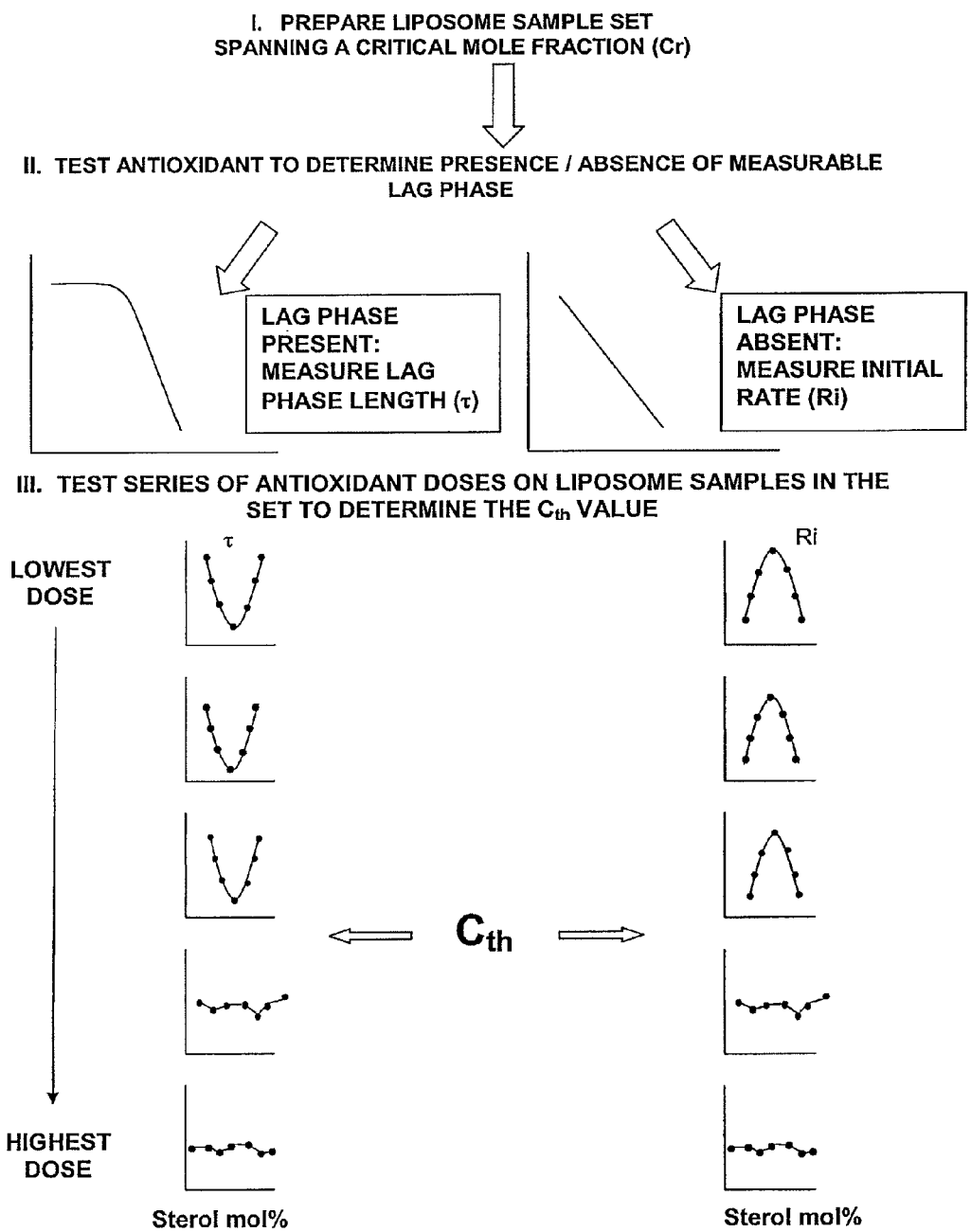
FIG. 9 shows a flowchart illustrating the method of the invention.

This invention provides a continuous, convenient, sensitive, reliable assay to assess simultaneously the potency and the possible adverse effect of antioxidants. The exemplary method of the invention is depicted in FIG. 9. The assay yields several quantitative parameters, the lag phase length ($\tau$) or the initial rate (Ri) and the threshold antioxidant concentration for superlattice disruption ($C_{th}$). The potential adverse effect is reflected in the $C_{th}$ value. It is believed that, the $C_{th}$ value is inversely proportional to the adverse effect of the antioxidant on cell membranes.

This assay could be used as a first-line screening method to identify potential antioxidants from natural products or synthetic compounds and also to rank both known and unknown antioxidants according to their ability to prevent oxidation of membrane sterol. This screening is of considerable commercial value because oxidized membrane sterol has been linked to the etiology of diseases such as coronary heart disease (57) and Alzheimer's Disease (58), and is also believed to cause many cytotoxic effects (58, 59). New and powerful anti-sterol oxidation agents are thus in high demand for prophylaxis or treatment purposes. Powerful antioxidants are often found in natural products such as green tea and curry powder. However, those kinds of natural food products typically contain thousands of different chemical compounds. There is a need to use a screening method to narrow down the number of candidates. The assay of the invention meets this need and can offer an economic and fast method to screen the potentially new and powerful anti-sterol oxidation antioxidants.

However, not all the powerful antioxidants are truly beneficial to human health; many of them could cause detrimental effects as mentioned earlier. In this regard, the assay is particularly appealing because it also has the capability to identify the potentially harmful antioxidants. When the assay is used to examine one particular lipophilic antioxidant as a function of sterol lateral organization, it is possible to get an estimate of the maximum threshold dose that may still confer antioxidant benefits. At doses above this threshold, perturbation of membrane lateral organization leads to disruption of the expected assay profile. Because so many properties and functions in cells are dependent upon or influenced by membrane lateral organization (51, 52, 53, 60), it is possible that the degree of disruption caused by higher doses of antioxidant overrides the potential benefits of radical scavenging at the site of the membrane.

After this initial screening, new and powerful, yet unharmful, antioxidants can be identified and selected for cell culture or animal tests, which are much more expensive and time consuming.

Even though the concept of sterol superlattice was introduced by inventors in 1994, it has not been applied to methods of screening antioxidants previously. While the spectroscopic and functional evidence for sterol superlattice to occur in the liquid-crystalline state (i.e., fluid state) of lipid bilayers is strong, most researchers in the membrane field still want to wait for the structure (e.g., neutron diffraction) or imaging (e.g., atomic force microscopy or other microscopies with atomic or molecular resolution) evidence for sterol superlattice formation to come out before they accept this model (or concept). However, because liquid-crystalline bilayer membranes and sterol superlattices are dynamic and fluid, the current technologies do not permit direct visualization or evidence for such structures at the atomic or molecular level.

Inventors have discovered that to demonstrate that the concept of sterol superlattice can be used to evaluate the potency and the possible adverse effect of an antioxidant, it is necessary to prepare many sets of vesicle samples that differ in the mole fraction of sterol by only a very small increment (~0.3%) and spread over a wide sterol mole fraction region.

Several critical and non-obvious ideas are required in order to come up with our invention even after knowing how to obtain a biphasic change of sterol oxidation rate at Cr in the absence of antioxidants (43). First, one needs to develop a method to quantitatively determine the potency of antioxidants. Second, one needs to realize that the potency of the antioxidant could vary with membrane lateral organization and membrane sterol content. Third, one needs to come up with the idea that the potency of the antioxidants should vary with membrane sterol content in a well-defined biphasic manner at specific sterol mole fractions, in accordance with the theory of sterol superlattice. Fourth, one needs to come up with idea that the antioxidants may attenuate sterol superlattice formation and that different antioxidants affect sterol superlattice differently. Fifth, one needs to come up with a method to quantitatively determine the threshold antioxidant dose that would be a measure of the antioxidant's ability to disrupt sterol superlattice. Sixth, one needs to come up with the idea that a disruption of sterol superlattice can cause an adverse effect on cells. These ideas and methods and how to integrate them to make an experimentally approachable assay are not obvious to others.

DEFINITION OF TERMS

The term "antioxidant" as used herein means a compound capable of defending the organism against free-radicals by acting as a scavenger. The antioxidant useful in this invention can be water-soluble, lipid-soluble or partly water soluble and partly lipid soluble.

The term "potency" as used herein means the strength of an antioxidant compound's radical-scavenging abilities. Antioxidant potency can be expressed as a function of its radical-scavenging abilities.

The term "critical dose ($C_{th}$)" as used herein means the threshold concentration of an antioxidant at which it begins to disrupt membrane lateral organization. $C_{th}$ is the threshold concentration of antioxidants, above which a biphasic profile of lag phase length ($\tau$) (or Ri) at $C_r$ is no longer discernible. $C_r$ is the theoretically predicted critical sterol mole fractions for maximal superlattice formation. In the sterol mole fraction range 19-53 mol %, the $C_r$ values are: 20.0, 22.2, 25.0, 33.3, 40.0 and 50.0 mol % sterol.

The term "fluorescent sterol probe" as used herein refers to a sterol molecule which can give rise to fluorescence upon excitation and has physical and physiological properties resembling cholesterol (the dominant sterol in animal cells) or ergosterol (the dominant sterol in yeast cells). Fluorescence can be measured, for example, at a wavelength of 396 nm+/−10 nm with excitation at 325 nm+/−10 nm.

Dehydroergosterol (DHE), a fluorescent cholesterol analogue, is a preferred fluorescent sterol probe because its physical and physiological behaviors resemble those found in cholesterol and it is capable of producing a detectable signal. Since it is a sterol, it is a membrane component. DHE can be excited by a range of wavelengths. The range follows its absorption spectrum. 325 nm is probably at or close to its absorption peak. When excited at the absorption maximum, the fluorescence intensity detected would be maximal. For this reason, inventors selected to excite DHE at 325 nm. It can also be excited at other wavelengths near 325 nm (e.g., 325 nm+/−10 nm). As long as DHE is exited in the right wavelength range, DHE can absorb the incident light and generate fluorescence. For this invention, the fluorescence intensity of DHE can also be observed at other wavelengths near 396 nm. This is because the fluorescence emission does not occur at a single wavelength; rather it occurs at a range of wavelengths, normally following a Gaussian distribution. Other non-fluorescent sterols, e.g., cholesterol or ergosterol can be mixed with DHE. As long as the total sterol mol % in the membrane reaches $C_r$, a biphasic change should occur. When describing the $C_r$ value, the term 'sterol mole percent" or "sterol mol %" and not "concentration" is used. When describing the $C_{th}$ value, the term "concentration" is used because the reference is made to the concentrations of the antioxidants.

The term "prooxidant" as used herein means a compound or atom, which induces oxidative stress, either through creating reactive oxygen species or inhibiting antioxidant systems. For example, the pro-oxidant 2,2'-azobis(2-amidinopropane) dihydrochloride (AAPH) creates reactive oxygen species (ROS), namely, peroxyl free radicals. This teen is used interchangeably with the term "free radical generator."

The term "lag phase" as used herein means the period of time after the addition of a prooxidant during which there is a slower rate of fluorescent sterol probe oxidation than there is in the absence of an antioxidant. During the lag phase, oxidation of fluorescent sterol probe already occurs but at a slower rate because free radicals are scavenged by antioxidant molecules at that time. After the scavenge process is over, the oxidation of fluorescent sterol probe becomes faster, thus creating a break point in the plot of F vs. time. The time between the addition of prooxidant (e.g., AAPH) and the occurrence of the break point is the lag phase. The lag phase length ($\tau$) is measured.

The term "Ri" as used herein means the initial rate of sterol oxidation in $sec^{-1}$. Ri can be calculated as follows: Ri equals [(Normalized fluorescence intensity of DHE at time t) minus (normalized fluorescence intensity of DHE at time 0)] divided by (t−0). Initial rate of sterol oxidation is calculated from the slope of DHE fluorescence intensity decrease vs time. By examining a typical plot, it is apparent that the first 15 minutes of sterol oxidation can be roughly fit to a straight line. However, a snapshot of the initial rate of oxidation at the very beginning of free radical production, before any change in lateral organization has occurred, is needed. Each sample set spanning a critical mole fraction must be analyzed separately in order to get an accurate picture for that particular set of vesicles. There are variations in the time used to define the initial rate calculation per sample set. One reason for these slight variations is due to the high sensitivity of fluorescence signals. Fluorescence intensity is a relative value, depending on the amount of fluorophore in the cuvette, sample mixing, temperature fluctuations, and quenching due to impurities in the sample. For this reason, each complete set is analyzed separately, but all sets are normalized so that they can be compared to each other. Each sample set is analyzed by examining the first five to ten minutes of fluorescence decay in a sequential manner. The first three minutes are plotted and then new plots are created for the first four, five, six, etc. minutes. The trend of the slopes of each sequential reaction profile shows the point at which the reaction rate first begins to slow. When the slope begins to become smaller in a systematic manner (meaning deviation from linearity), then the data points at shorter time should be used. By looking at the reaction profiles in this fashion, details are visible that would be overlooked if the larger profile only was examined. It is possible to visualize the beginning of deviation from linearity, which usually occurs between four and seven minutes, depending on the sample set. Within a sample set, the deviation from linearity can be determined, and the number of minutes that will be used to calculate the initial rate can be defined. An acceptable linear fit for that particular time span is usually a correlation coefficient (R) value of at least 0.8. However, the validity of a particular R value is based on a power analysis, which takes into account the sample size and calculates the lowest acceptable correlation coefficient that will still give a 95% confidence interval (p<0.05). The correlation coefficient can be somewhat lower than would normally be accepted because its value is based not only on the spread of points, but on the number of points in the plot. If one choose an initial rate for the first five minutes, the Ri values may be systematically lower than those for a set where the initial rate is defined as the first six minutes. The initial rate is defined as the smallest time frame that gives a linear plot and a reasonable correlation coefficient and power analysis.

Biphasic effect can be determined as follows. In the plot of lag phase ($\tau$) (or Ri ($sec^{-1}$)) versus sterol mol %, a curve is called biphasic if the following conditions are met: (1) there is a local minimum or maximum in $\tau$ (or Ri) at certain sterol mole fractions (ideally these mole fractions are the $C_r$ values), (2) there are more than one data point on either side of the local min or max; (3) the depth or height of a biphasic change is significantly greater than the standard deviation of $\tau$ (or Ri).

Description of the Membrane Model System

A membrane model system of the invention (i.e, a unilamellar vesicle) comprises a fluorescent sterol probe, a bilayer forming lipid (e.g., a phospholipid) and optionally a spacing lipid (e.g., cholesterol and glycolipids (e.g., gangliosides). These components are added together to form large unilamellar vesicles (LUVs).

Preferably, the concentration of sterol in the fluorescent sterol probe is varied from 19 mol % to 52 mole %. There are several theoretically predicted $C_r$ values (namely, 20.0, 22.2, 25.0, 33.3, 40.0, and 50.0 mol %) in the sterol mol % range 19-52 mol %. A typical sample set contains between nine and fifteen independently prepared samples, each one increasing in mole percent of sterol by a very small increment (~0.3 mol %). The absolute amount of sterol remains constant from sample to sample; the mole fraction of sterol is varied by changing the amounts of the non-sterol lipid components in small increments from sample to sample. The end result is a series of samples in which the mol % of sterol changes by small steps over an entire range of less than 3-4 mol %. Because the absolute number of sterol molecules remains constant throughout the sample set, differences in the rate of sterol oxidation and the length of the antioxidant-induced lag phase can only be attributed to differences in sterol mole percent (hence, differences in sterol lateral organization in the bilayer). Sterol oxidation was initiated by a peroxy radical generator AAPH.

The following Table gives an example:

| tube # | Sterol mol % | DHE nmol | POPC nmol |
|---|---|---|---|
| 1 | 18.4 | 125 | 554 |
| 2 | 18.8 | 125 | 540 |
| 3 | 19.1 | 125 | 529 |
| 4 | 19.4 | 125 | 519 |
| 5 | 19.7 | 125 | 510 |

-continued

| tube # | Sterol mol % | DHE nmol | POPC nmol |
|---|---|---|---|
| 6 | 20.0 | 125 | 500 |
| 7 | 20.3 | 125 | 491 |
| 8 | 20.6 | 125 | 482 |
| 9 | 20.9 | 125 | 473 |
| 10 | 21.2 | 125 | 465 |
| 11 | 21.5 | 125 | 456 |

In this sample set, 20.0 mol % sterol is the only predicted critical sterol mole fraction $C_r$ for maximal superlattice formation. The range is 18.4-21.5 mol %. To prepare this set of samples (with $C_r$=20.0 mol %), 18.5 and 21.5 mol % would be employed as the lower and upper sterol mole fractions. But if a sample set spanning $C_r$=25.0 mol % is used, these numbers will be changed to 23.5 and 26.5 mol %. The suggested range will be at least $C_r \pm 1.5$ mol %. But, if time and energy are allowed, the range may be increased to, for example, $C_r \pm 1.8$ mol %. Then more samples will be involved in each set. For example, if the range is extended to $C_r \pm 1.8$ mol % for the sample set around $C_r$=20.0 mol % (similar to that in the table), then one would need to make the following sample tubes in order to cover the range $C_r \pm 1.8$ mol %. The sample tubes in this new set will be 18.2, 18.5, 18.8, 19.1, 19.4, 19.7, 20.0, 20.3, 20.6, 20.9, 21.2, 21.5, 21.8, mol % sterol.

The molar ratio of bilayer forming lipid (e.g., a phospholipid) to sterol (including fluorescent sterol probe) can be varied from 0.67 to 5.6; preferably from 0.92 to 4.6.

The mol % of the spacing lipid can be from 18 to 51.

The membrane model system can be two-component or a multi-component system. An exemplary two-component membrane model system includes DHE and 1,2-dimyristoyl-sn-glycero-3-phosphocholine (DMPC).

An exemplary multi-component system is DHE+cholesterol+DMPC. In this case, the x-axis is the total sterol mol %. As long as the total sterol mol % reaches the value $C_r$, there will be a biphasic change. Total sterol mol %=DHE mol %+cholesterol mol %. The membrane system can also be extended to include other lipids (e.g., cholesterol and other non-phospholipids such as gangliosides).

The model system can be prepared at the time of assay or can be prepared beforehand and stored in the dark as liposomes in buffer in sealed tubes at room temperature or in the refrigerator.

Description of the Method of the Invention

In one aspect, the invention is a method of screening an antioxidant for potency and/or toxicity in vitro, the method includes contacting the antioxidant with a model system comprising a sterol superlattice formation capable of generating a detectable signal, wherein the detectable signal changes in a parameter representative of an integrity of the sterol superlattice formation; and detecting and/or measuring disruption of the sterol superlattice formation, wherein the disruption is caused by oxidation of sterol upon contacting sterol with a prooxidant and the antioxidant and thereby screening the antioxidant for potency and/or toxicity.

In another aspect, the invention is a method to determine potency of an antioxidant or a critical dose of an antioxidant in vitro based on the disruption of a sterol superlattice formation. The method includes (a) providing a fluorescent sterol probe, a bilayer forming lipid (e.g., a phospholipid) and optionally a spacing lipid (e.g., cholesterol and glycolipids (e.g., gangliosides) to form unilamellar vesicles, wherein a concentration of sterol in the fluorescent sterol probe is varied from 18 mol % to 52 mole %; (b) providing an antioxidant; (c) providing a prooxidant; (d) combining the unilamellar vesicles, the antioxidant and the prooxidant; (e) measuring (1) the sterol fluorescence intensity from the time of the addition of the prooxidant to at least five minutes after the time of an abrupt change in sterol oxidation rate, and thereby obtaining a lag phase length (t), or (2) the sterol fluorescence intensity from the time of the addition of the prooxidant to the time when the fluorescence intensity vs. time begins to deviate from linearity, and thereby obtaining a Ri value. The linearity should show a correlation coefficient value of at least 0.8 with a confidence interval of at least 95%; (f) plotting the lag phase length ($\tau$), or the initial rate (Ri) as a function of the total sterol mole fraction to detect a biphasic effect; and (g) repeating said measuring at increasing doses of the antioxidant to determine the threshold concentration ($C_{th}$) at which the biphasic effect substantially disappears.

The assay to obtain $C_{th}$ was tested on model systems consisting of two-component (PC/DHE) large unilamellar vesicles (LUVs). This assay should also work in three-component (PC/DHE/cholesterol) or multi-component (e.g., porcine brain sphingomyelins/PC/DHE) LUVs. This assay can be extended to work with lipoprotein particles and cells, provided that the fluorescent cholesterol analogue, DHE, has first been incorporated into the membrane.

One limiting factor would be if the antioxidant itself were fluorescent, with excitation and emission wavelengths significantly overlapping with those for DHE. In this rare case, a careful scrutiny of the excitation and emission properties such as fluorescence lifetime and anisotropy may shed light on how to use spectroscopy to differentiate the signals from DHE from those from the fluorescent antioxidant.

A second limiting factor would be an inability to solubilize the antioxidant in water or in mild organic solvents. To overcome this problem, one could dissolve both the antioxidant and the lipids in strong organic solvents (e.g., chloroform), mix them in appropriate proportions, and then make lipid films. The dried lipid film is then dispersed in warm buffer with vigorous agitation for vesicle formation.

Figure 8:
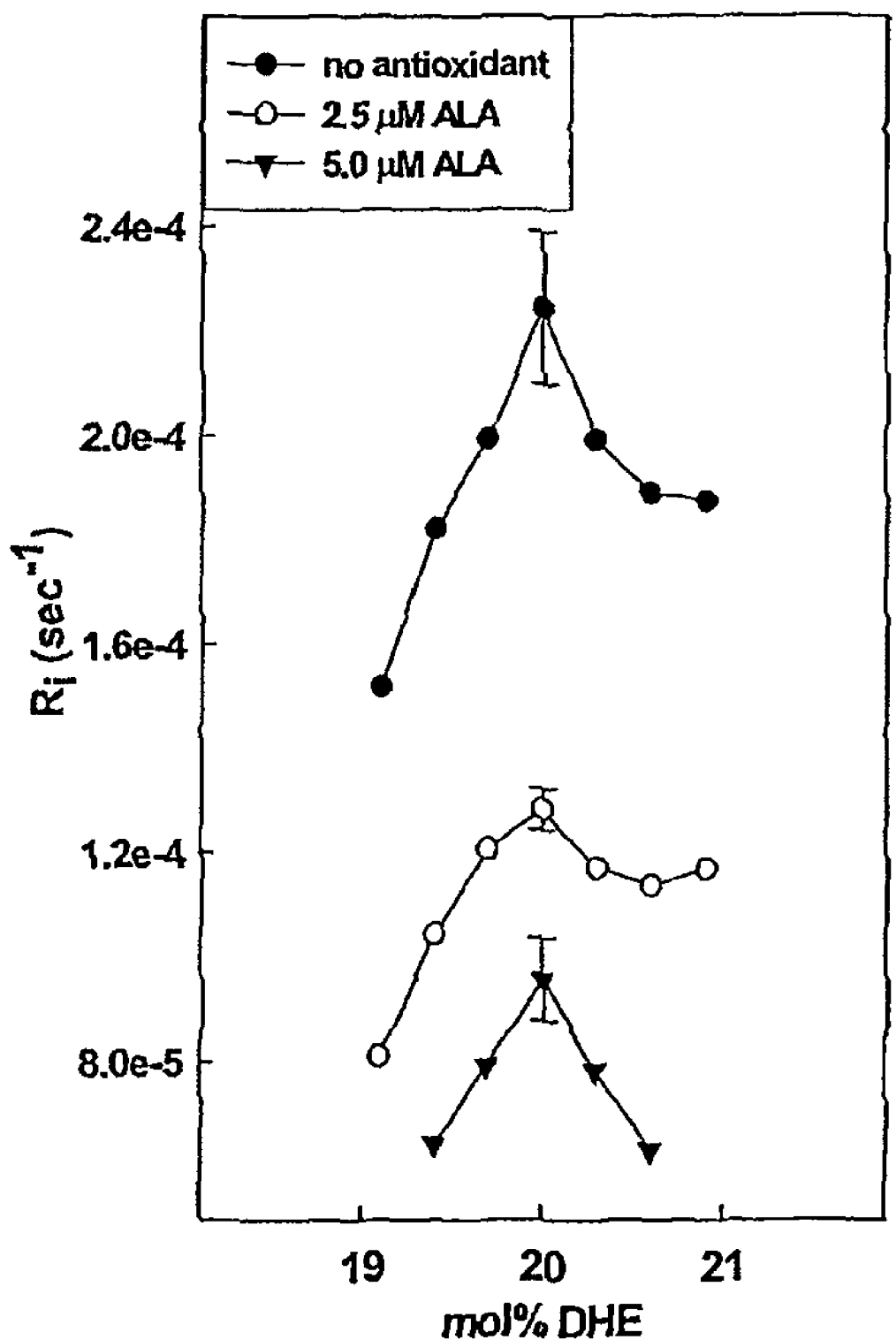
FIG. 8 illustrates the usefulness of our assay when the antioxidant (e.g., alpha lipoic acid (ALA)) does not produce a lag phase in the AAPH-induced DHE fluorescence decay. The main purpose of this assay is to determine the $C_{th}$ value for the antioxidant ALA, which is both water and lipid soluble. Although ALA does not generate a lag phase in the AAPH-induced sterol oxidation assay, it shows an antioxidant activity in terms of a decrease in the initial rate of sterol oxidation (Ri). Ri came from monitoring DHE fluorescence intensity after addition of AAPH. Ri decreases with increasing ALA doses (data not shown), which indicates that ALA acid has an anti-sterol oxidation activity. In this case (the right panel in the flow chart—FIG. 9), the initial rate of sterol oxidation (Ri), instead of the lag phase, is used as the parameter to reflect the potency of an antioxidant activity. In the absence of ALA (dark circles), Ri exhibits a biphasic change with sterol content, showing a local maximum at $C_r$ (20.0 mol % in this case). The membrane system is: 1-palmitoyl-2-oleoyl-L-α-phosphatidylcholine (POPC)/porcine brain sphingomyelins (pSPMs)/DHE LUVs. This biphasic change is expected from the sterol superlattice theory and is consistent with our previous finding (43). In the presence of ALA (open circles for 2.5 mM and dark triangles for 5.0 mM), the biphasic change profile is retained, meaning that lipoic acid up to 5.0 mM does not abolish sterol superlattice in the POPC/pSPMs/DHE bilayer membrane. In this case, the $C_{th}$ value is determined to be >>5 mM, if there is any. Vertical bars are the standard deviations from three independently prepared samples. The experiment was carried out at 37-42° C.

Two-component or multi-component models of large unilamellar vesicles (LUVs) containing DHE (dehydroergosterol) are prepared as described above. The sizes of LUVs are in the range of 100-800 nm in diameter. [Please quantify the term "large"]. A prooxidant or a free radical generator is added to a fluorescence cuvette containing LUVs that have been incubated with an antioxidant. In certain embodiments, sterol oxidation was induced by a water-soluble free radical generator, AAPH (2,2'-azobis(2-amidinopropane) dihydrochloride). Time trace monitoring reveals either an antioxidant-induced lag phase ($\tau$) (period of slower oxidation of DHE), followed by a period of fast oxidation once the antioxidant has been depleted, or simply a dose-dependent decrease in the rate of DHE oxidation without displaying a lag phase. Plotting the lag phase length ($\tau$) (or the initial rate Ri, in the case of lacking lag phase) vs sterol mole fraction in the presence of low dose antioxidant, a biphasic change in (or Ri) at a given $C_r$ (e.g., 20.0, 22.2, 25.0, 33.3, 40.0 and 50.0 mol % sterol) is observed (see FIGS. 4, 8, and 9). This experiment will be repeated at different antioxidant doses. A threshold antioxidant concentration ($C_{th}$) is the highest antioxidant concentration at which the biphasic change in $\tau$ with sterol mol % may still be detected. The $\tau$, Ri, and $C_{th}$ values will give information about the antioxidant activity or potency and side effects. The $\tau$ and Ri values will give information about the antioxidant activity or potency. The higher the $\tau$ value is, the more potent the antioxidant will be. The ratio of the Ri value in the presence of antioxidants to that in the absence of antioxidants (Ri/Rio) also reflects the potency of the antioxidant. The smaller the (Ri/Rio) value is, the more potent the antioxidant will be. For the antioxidants (e.g., ascorbic acid and ascorbyl palmitate) that scavenge free radicals at a rate faster than or comparable to the rate of free radical-induced sterol oxidation, a lag phase will appear and the lag phase length ($\tau$) will be used to reflect the potency of the antioxidant. For the antioxidants (e.g., alpha-lipoic acid) that scavenge free radicals at a rate significantly slower than the free radical-induced sterol oxidation, a lag phase will not appear and in this case the initial rate Ri will be used to measure the potency of the antioxidant. The $C_{th}$ value indicates the potential toxicity of the antioxidant. The lower the $C_{th}$ value is, the higher the potential damage to cell membranes becomes. The $C_{th}$ values will be determined based on the capability of the antioxidant to abolish the biphasic change of either $\tau$ or Ri with membrane sterol mole fraction. All of the antioxidants, either producing $\tau$ or Ri, can be compared and ranked based on the $C_{th}$ values.

The lag phase length ($\tau$) produced by either ascorbic acid or ascorbyl palmitate in 1,2-dimyristoyl-sn-glycero-3-phosphocholine (DMPC)/DHE large unilamellar vesicles (LUVs) as a function of sterol mole fraction in three sets of samples spanning three predicted critical mole fractions (Cr) (i.e., 20.0, 25.0, and 40.0 mol % sterol) has been studied. For each set, ascorbic acid, which is water-soluble, demonstrated a biphasic change in lag phase length at all tested doses. Lipid-soluble ascorbyl palmitate, however, only produced a biphasic profile in samples receiving a relatively low dose of antioxidant. At higher doses of ascorbyl palmitate, the profile was disrupted or obliterated. All the ascorbyl palmitate sample sets together revealed a threshold level ($C_{th}$), above which the profile of lag phase was no longer predictable. Because ascorbyl palmitate is lipophilic, higher doses probably lead to a significant degree of membrane perturbation. This possibility was tested by measuring DHE fluorescence anisotropy as a function of antioxidant concentration. All the data suggest that partitioning of ascorbyl palmitate into the lipid bilayer disrupts sterol superlattice formation. It is believed that membrane perturbation, as evidenced by the disruption of sterol superlattice, may contribute significantly to the detrimental effects of lipid-soluble antioxidants reported in recent clinical studies.

The method of the invention will now be described using a two-component model as an example.

Dehydroergosterol (DHE; Sigma, St. Louis, Mo.) was first purified by HPLC, and then dissolved in $CHCl_3$ to make a stock solution. The concentration of DHE stock solution was calculated by absorbance in dioxane at 326 nm, using an extinction coefficient equal to 10,600 $M^{-1}$ $cm^{-1}$. DMPC was purchased from Avanti Polar Lipids (Alabaster, Ala.). The concentration of DMPC in stock solution and in LUVs was determined by the method of Bartlett (61). The prooxidant AAPH ((2,2'-azobis(2-amidinopropane) dihydrochloride) was obtained from Aldrich (Milwaukee, Wis.). Ascorbic acid and ascorbyl palmitate were purchased from Sigma.

Calculated amounts of DMPC and DHE were pipetted into tubes and dried under $N_2$ until there was no visible solvent; lipids were then dried overnight under vacuum. Next, lipids were reconstituted at 37° C. with 5.0 mL of 50 mM Tris-HCl buffer at pH 7.0 (containing 0.02% $NaN_3$ and 0.1 mM EDTA), then flushed with $N_2$, and vortexed for 2 min at 37° C. to form multilamellar vesicles (MLVs). The MLVs were cooled to 4° C. for 30 min and then incubated at 37° C. for 30 min. This cooling/heating cycle was repeated three times to ensure an even distribution of lipids within each monolayer of the vesicles. After being exposed to three cycles of heat/cold to allow for thorough mixing, vesicles were left for 4 days at room temperature to come to thermal equilibrium. LUVs were then prepared from MLVs by extrusion (Lipex Biomembranes Inc., Vancouver, BC, Canada). The MLVs were extruded at 37° C. 10 times through two stacked 200 nm Nucleopore polycarbonate filters (Costar) under nitrogen gas pressure to form homogeneous LUVs. To avoid auto-oxidation of sterol, the LUV samples were flushed with argon, sealed, and stored in a dessicator chamber under vacuum at room temperature for seven days prior to sterol oxidation measurements (50). During this time, phosphorus concentration was measured again to determine new phospholipid concentration after loss by extrusion (53).

A typical LUV sample set spanned a predicted critical sterol mole fraction ($C_r$) for maximal superlattice formation. Every sample within the set contained the same absolute amount of sterol; only the sterol mole percent was changed by small increments. This was accomplished by varying the number of moles of phospholipids per tube, while leaving the number of moles of sterols constant.

Calculated amounts of LUVs, Tris-HCl buffer and antioxidant were added to reaction cuvette and incubated under gentle magnetic stirring for 15 min at 37° C. in the sample compartment of the SLM 8000C fluorometer (Urbana, Ill.). After incubation, time trace monitoring was begun. Excitation wavelength was 325 nm with a band-pass of 0.5 nm. Emission of DHE fluorescence was observed at 396 nm through a monochromator with a band-pass of 8 nm. 30 µL of 300 mM freshly prepared AAPH was added to initiate sterol oxidation (43).

Steady-state anisotropy measurements were made at 37° C. on an ISS K2 fluorometer (ISS, Champaign, Ill.). Excitation wavelength used was 325 nm, with a bandwidth of 8 nm. Emission was measured through a KV-408 filter with $\lambda_{ex}$=399 nm. Blank readings from membranes without probes were subtracted from the sample readings.

Figure 1:
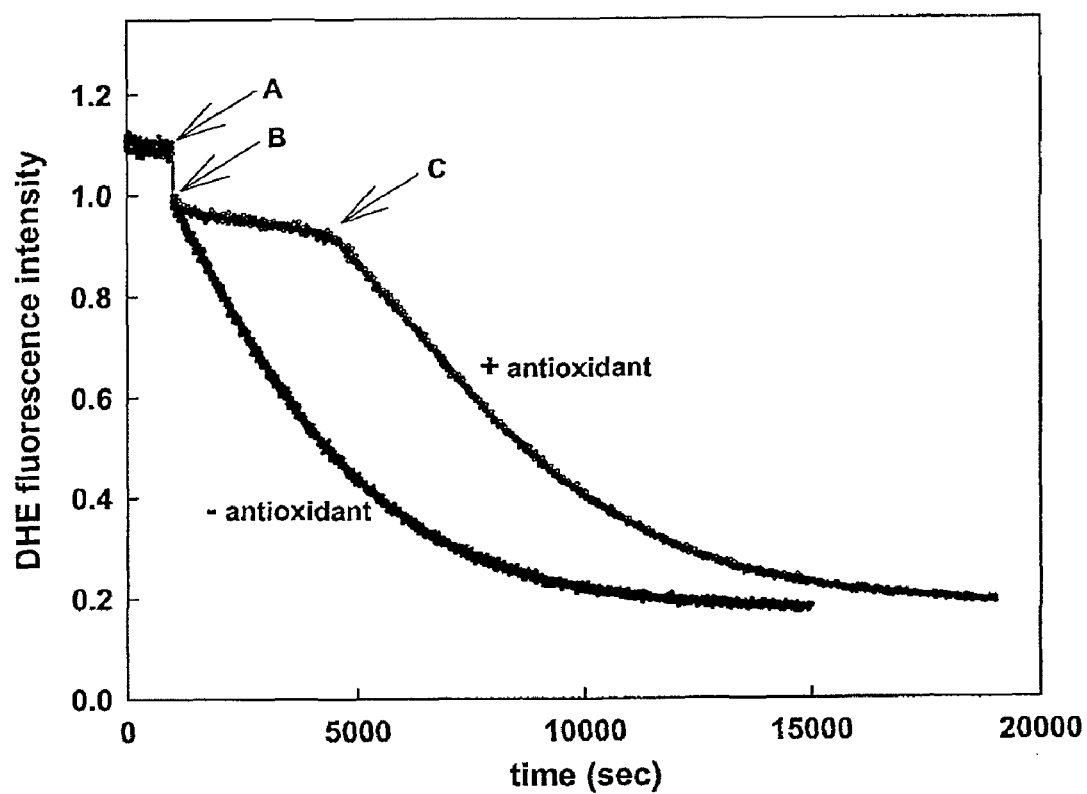
FIG. 1 shows the time trace monitoring of dehydroergosterol (DHE) fluorescence intensity decrease in 1,2-dimyristoyl-sn-glycero-3-phosphocholine (DMPC)/DHE large unilamellar vesicles (LUVs) with and without antioxidant.

The fluorescence assay uses DHE both as a membrane probe and as a membrane component. The fluorescence intensity of DHE decreases upon AAPH-induced oxidation, so the rate of sterol oxidation in the presence or absence of an antioxidant can be measured (FIG. 1).

Figure 2:
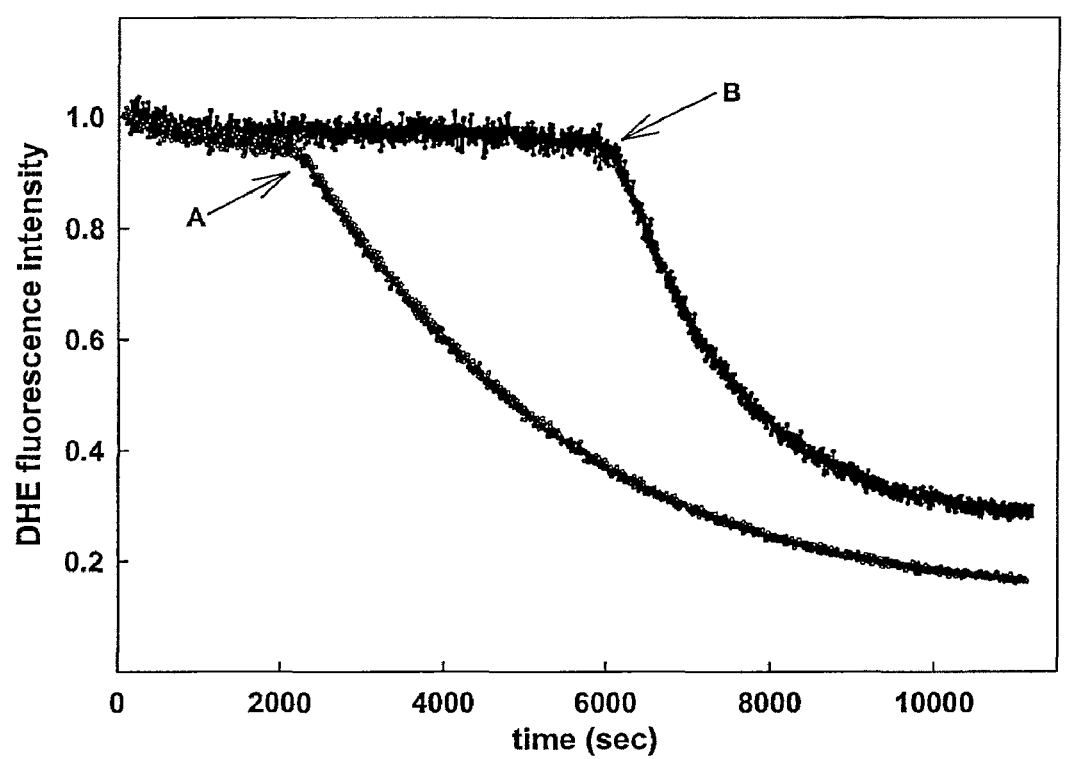
FIG. 2 shows the comparison of the time trace of free radical-induced DHE fluorescence intensity decrease in the presence of water-soluble (A) and lipid-soluble (B) vitamin C. Lag phases were induced by both antioxidants.
Figure 3:
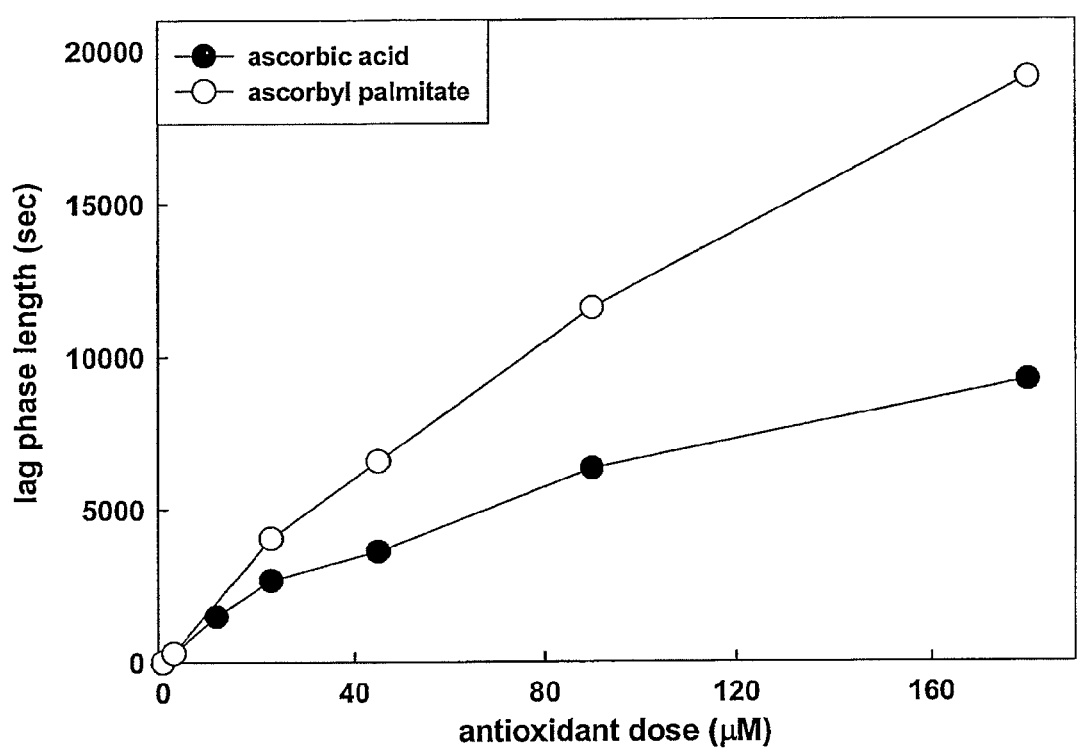
FIG. 3 shows the dose dependence of the lag phases induced by ascorbic acid and ascorbyl palmitate. The plot shows a comparison between the length of the lag phases produced by ascorbic acid and by ascorbyl palmitate. At the same apparent dose, ascorbyl palmitate is much more potent in protecting against sterol oxidation than its water-soluble counterpart, ascorbic acid.

To compare differences in the effects of hydrophilic vs lipophilic antioxidants, two forms of vitamin C, ascorbic acid (water-soluble) and ascorbyl palmitate (lipid-soluble) we selected. Monitoring fluorescence intensity decrease of DHE (due to prooxidant, AAPH) in the presence of either antioxidant, an antioxidant-induced lag phase (FIG. 1) was observed. The lag phase is a period of slow oxidation during which the antioxidant is scavenging some proportion of the free radicals being generated. Once the antioxidant has been depleted, the rate of sterol oxidation increases. Lag phase length is a measure of the antioxidant ability of a substance. The lag phase induced by ascorbyl palmitate is about three times longer than that induced by the same apparent dose of ascorbic acid (FIGS. 2 and 3).

From the data of lag phase, it would seem that ascorbyl palmitate is a more powerful antioxidant than is ascorbic acid, and can better protect membrane sterol from oxidation than can a water-soluble antioxidant. However, when a single dose of antioxidant was used and the sterol mole percent was varied, a different picture was observed. Because of the experimental design, all samples in a set vary only in the mole fraction of sterol, not in the absolute number of sterol molecules. Therefore, one would expect that the relative potency of the antioxidant (measured as length of lag phase) should be the same from sample to sample. If the variation is predictable, and changes biphasically at the theoretically predicted critical mole percent ($C_r$), then our data is in full support of the sterol superlattice theory and demonstrates the importance of membrane lateral organization. Differences in lateral organization of membrane components cannot be visualized directly; here, we use the appearance of predictable, biphasic changes in lag phase length at $C_r$ as evidence of sterol superlattice formation, and as a tool to examine the effect of lateral organization on the potency of an antioxidant.

At a predicted critical mole fraction of sterol ($C_r$), the sterol molecules are more accessible to the aqueous phase, hence are more susceptible to oxidation. The greater accessibility is due to tighter packing of membrane components in the regular region, compared to that in the irregular region (47). Differential packing in the regular region may cause sterol to be embedded less deeply in the bilayer, and/or may cause the polar head groups to adopt a different conformation, thereby exposing the sterol molecule (62). A third possibility that may result in greater sterol accessibility is the sudden increase in interfacial surface area (border between regular and irregular regions) at $C_r$ (50). Interfacial sterol molecules may then be more exposed to the aqueous oxidizing agent. Although the actual physical position of the membrane components cannot be visualized, it is predicted that the length of the antioxidant-induced lag phase will be proportional to the accessibility of the sterol molecules; the more sterol is exposed to the oxidizing agent, the less effective the antioxidant will be.

The same method, with a minor modification, can also be applied to the antioxidants that do not produce a lag phase for sterol oxidation. This is the case for the antioxidant alpha lipoic acid (ALA). ALA does not generate a lag phase for sterol oxidation; however, it produces a dose-dependent decrease in the initial rate (Ri) of sterol oxidation (Yoon and Chong, unpublished results). In this case, the plot of Ri vs mol % sterol shows an alternating variation in sterol-containing lipid membranes, with the highest initial rate occurring at a critical mole fraction ($C_r$) of sterol, as predicted by the sterol superlattice theory. By comparing the Ri-vs-mol % sterol profiles at different antioxidant doses, we can determine $C_{th}$ at which the membrane-soluble antioxidant begins to disrupt membrane lateral organization.

Calculated amounts of POPC, porcine brain sphingomyelins, and DHE were pipetted into test tubes, mixed and dried under $N_2$ until there was no visible solvent. Lipids were then dried overnight under vacuum. Next, lipids were reconstituted at 67° C. with 5.0 ml of 0.02% $NaN_3$, 0.1 mM EDTA, 50 mM Tris-HCl buffer (pH 7.0). The lipid dispersions were then flushed with $N_2$, and vortexed for 3 min at 67° C. to form multilamellar vesicles (MLVs). The MLVs were cooled to 4° C. for 30 min and then incubated at 67° C. for 30 min. This cooling-heating cycle was repeated three times to ensure an even distribution of lipids within each monolayer of the vesicles. Vesicles were left for 7 days at room temperature under the vacuum chamber to come to thermal equilibrium. LUVs were then prepared from MLVs by using the extrusion method mentioned earlier.

The stock solution of lipoic acid in ethanol was freshly prepared. 30 µl of lipoic acid solution was added to a cuvette containing 1.6 mL LUVs composed of DHE(120 nmol)/POPC/porcine brain sphingomyelins in Tris buffer. The mixture was incubated for 15 min at 37 or 42° C., prior to the addition of AAPH. 30 µl of 300 mM AAPH was added to the cuvette to trigger the oxidation reaction. The DHE fluorescence intensity was then monitored over time.

Membrane lateral organization and domain formation play an important role in many cellular activities, such as sorting of membrane proteins and lipids, activity of surface-acting enzymes, signal transduction, protein stabilization and membrane fusion (51, 53, 60, 63, 64). The sterol superlattice model describes how minute changes in the mole fraction of sterol in the membrane can lead to large-scale reorganization of membrane components. This abrupt shift in membrane lateral organization at certain theoretically predicted mol % values cannot be visualized directly. However, these changes in sterol lateral organization may be monitored by measuring other properties as a function of sterol mol %. For example, inventors have demonstrated that the activities of some membrane surface-acting enzymes show a predictable, biphasic change in initial rate as a function of sterol mol % (52, 53). In addition, the partitioning of the antifungal drug, nystatin, varies with membrane sterol content in an alternating manner (51). Recently, it was shown that free-radical induced oxidation of membrane sterol can also give information about membrane lateral organization (54). In all of the examples cited, a small change in sterol mole fraction, which allows the membrane to reach a theoretically predicted critical mole fraction of sterol, leads to an abrupt shift in the lateral organization of membrane components and a concomitant change in membrane packing. Due to the immediate global changes in membrane packing, the availability of membrane sterol also changes. Sterol molecules are more accessible to the aqueous phase at $C_r$, when compared to sterol molecules at non-$C_r$. In this case, it would follow that the rate of sterol oxidation would be faster at $C_r$, when sterol molecules are more visible to aqueous phase free radicals.

When LUVs are incubated with an antioxidant, a measurable lag phase is produced; the length of this lag phase is a relative estimate of antioxidant potency.

Figure 4:
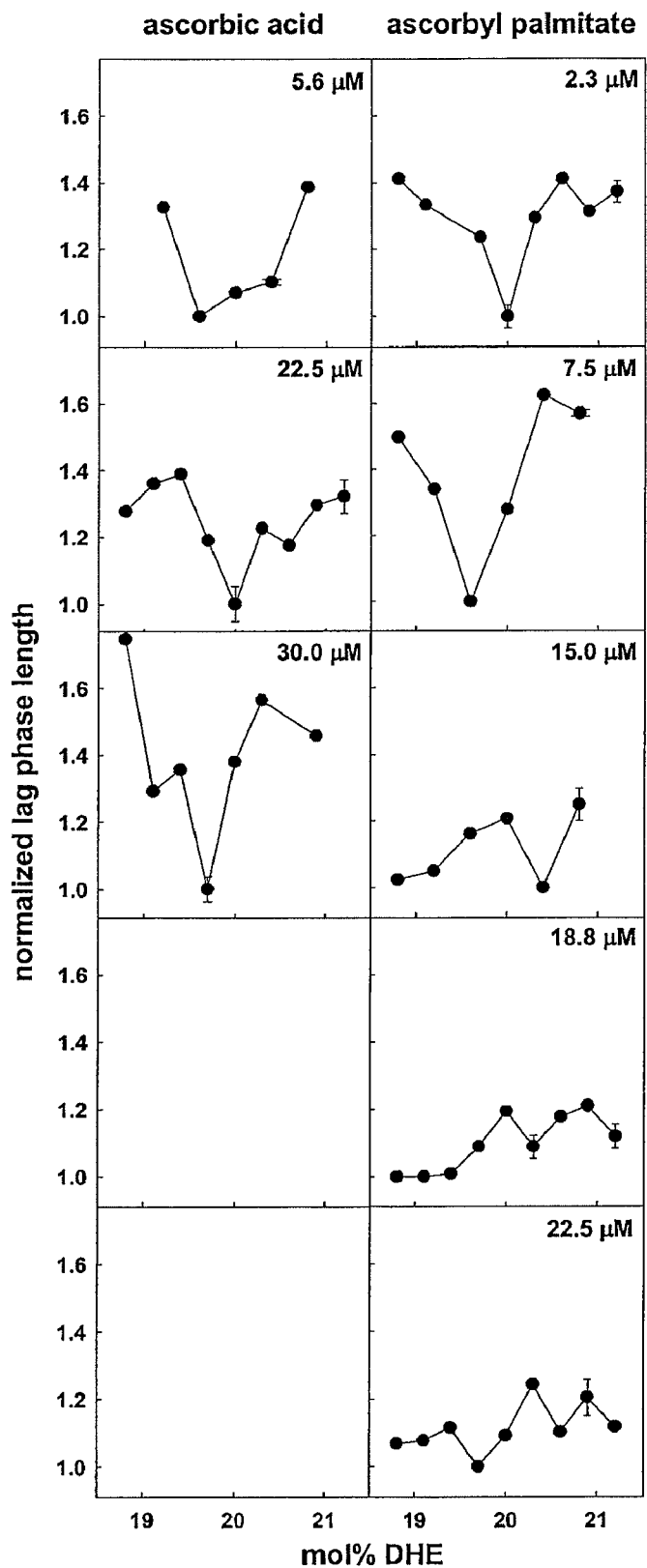
FIG. 4 shows the normalized lag phase length vs mol % DHE. The sample set spans predicted $C_r$ of 20.0 mol % DHE. Left panel: ascorbic acid doses ranged from 5.6 µM to 30.0 µM; in each of these experiments, a biphasic change in lag phase length is apparent. The shortest lag phase occurred at or near (within 0.4 mol %) $C_r$. Right panel: ascorbyl palmitate doses ranged from 2.3 µM to 22.5 A biphasic change is evident only in sample sets incubated with 2.3 µM and 7.5 µM ascorbyl palmitate. At concentrations of 15.0 µM and above, the biphasic profile is obliterated. Vertical bars are the standard deviations calculated from three independent experiments.
Figure 5:
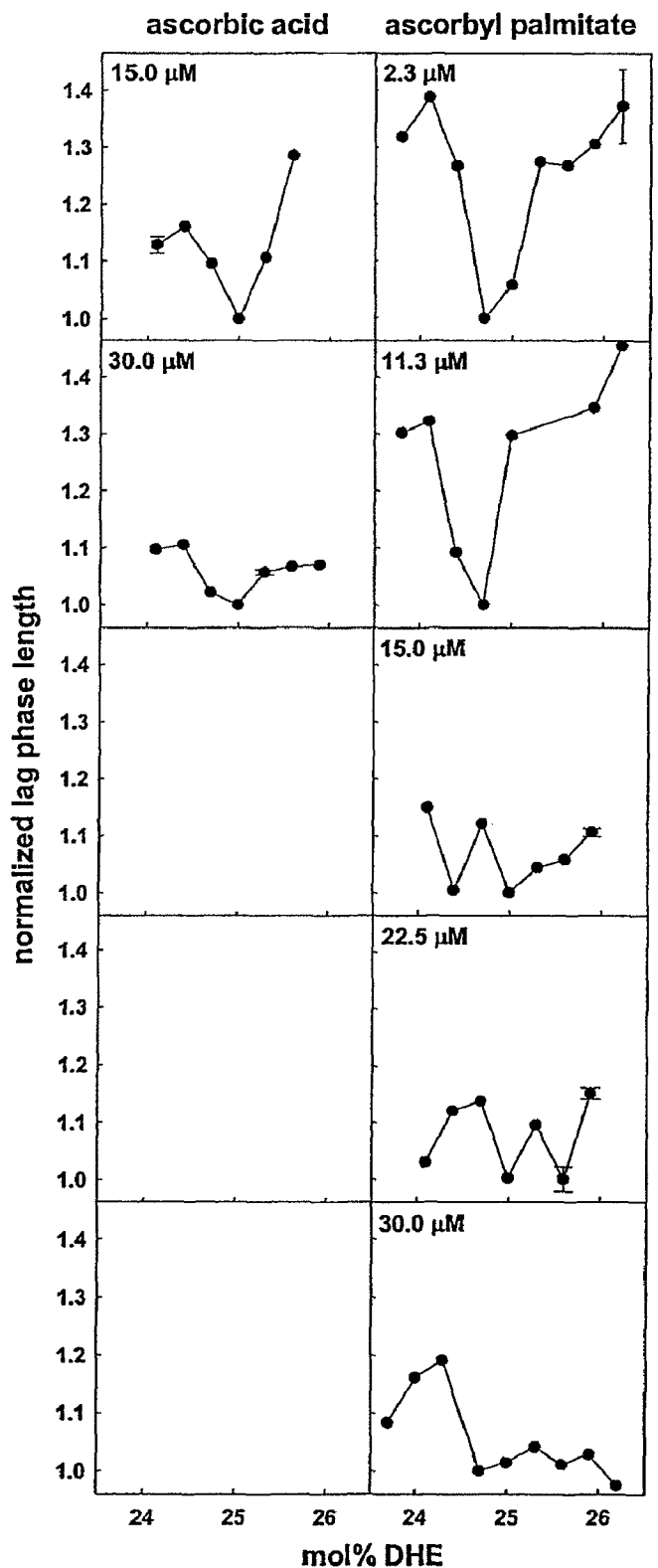
FIG. 5 shows the normalized lag phase length vs mol % DHE. The sample set spans predicted $C_r$ of 25.0 mol % DHE. Left panel: ascorbic acid doses ranged from 15.0 to 30.0 µM; Right panel: ascorbyl palmitate doses ranged from 2.3 to 30.0 µM. A biphasic change is evident only in sample sets incubated with 2.3 µM and 11.3 µM ascorbyl palmitate. At concentrations of 15.0 µM and above, the biphasic profile is obliterated. Vertical bars are the standard deviations calculated from three independent experiments
Figure 6:
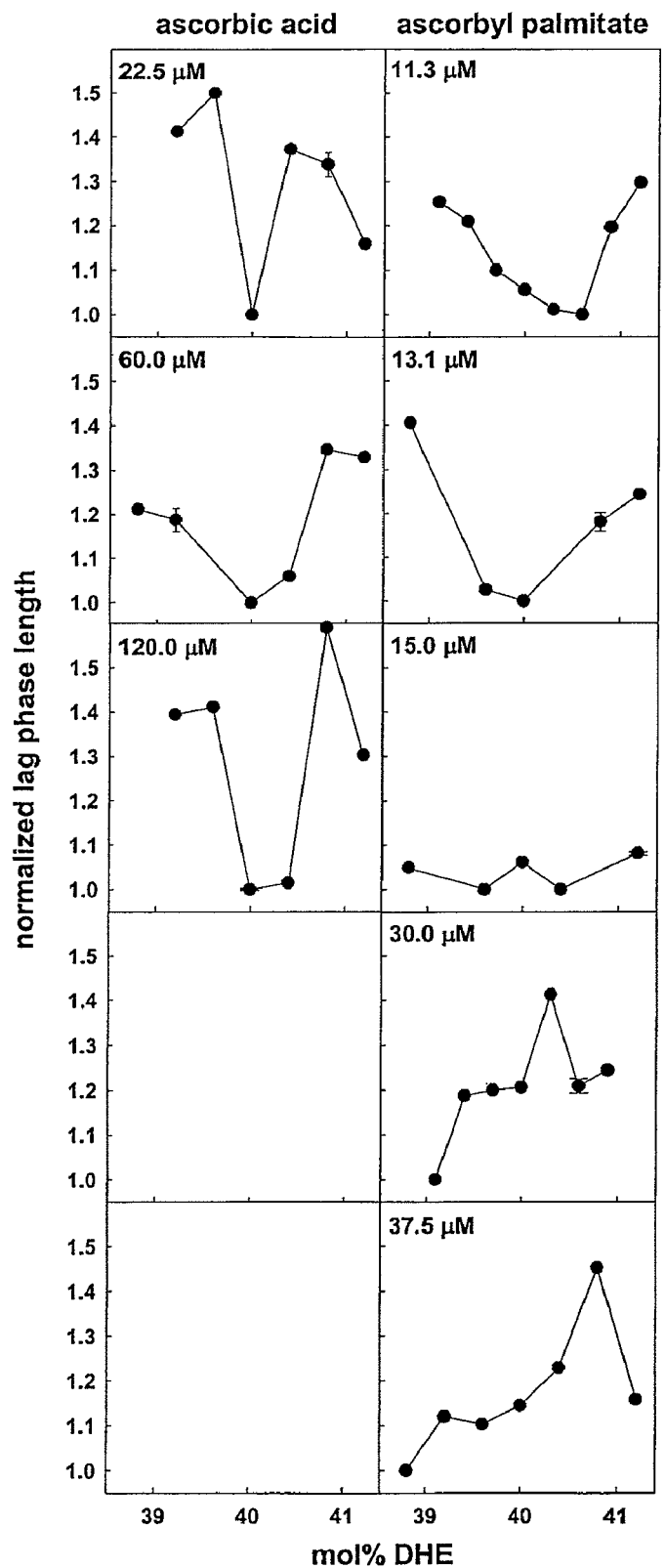
FIG. 6 shows the normalized lag phase length vs mol % DHE. The sample set spans predicted $C_r$ of 40.0 mol % DHE. Left panel: ascorbic acid doses ranged from 22.5 µM to 120.0 µM; in each of these experiments, a biphasic change in lag phase length is apparent. The shortest lag phase occurred at or near (within 0.4 mol %) $C_r$. Right panel: ascorbyl palmitate doses ranged from 11.3 µM to 37.5 µM. A biphasic change is evident only in sample sets incubated with 11.3 µM and 13.1 µM ascorbyl palmitate. At concentrations of 15.0 µM and above, the biphasic profile is obliterated. Vertical bars are the standard deviations calculated from three independent experiments.

When ascorbic acid is added to LUV samples differing in sterol mol % by small increments, a biphasic profile of lag phase length vs mol % sterol is produced. Ascorbic acid is a hydrophilic antioxidant, and is able to scavenge free radicals in the aqueous phase. If sterol is more accessible at $C_r$, then we might expect more efficient oxidation of sterol at $C_r$. This is reflected in the length of the ascorbic acid-induced lag phase, which is shorter in duration at or near $C_r$. In FIGS. 4, 5 and 6, the left-hand panels show alternating changes in lag phase length as a function of mol % sterol at all ascorbic acid concentrations tested. This indicates that the water-soluble ascorbic acid has virtually no effects on sterol lateral organization.

Experiments were also performed using ascorbyl palmitate, the lipid-soluble form of vitamin C. A biphasic profile of lag phase length vs mol % sterol was generated when a low antioxidant dose was used. However, ascorbyl palmitate shows a break point where the biphasic profile in lag length is disrupted; at concentrations above 15 µM in all sample sets tested, the biphasic profile was attenuated or obliterated. At sufficiently high concentrations of the lipophilic antioxidant, membrane lateral organization is disturbed by insertion of the antioxidant into the membrane, and the results become randomized.

Figure 7:
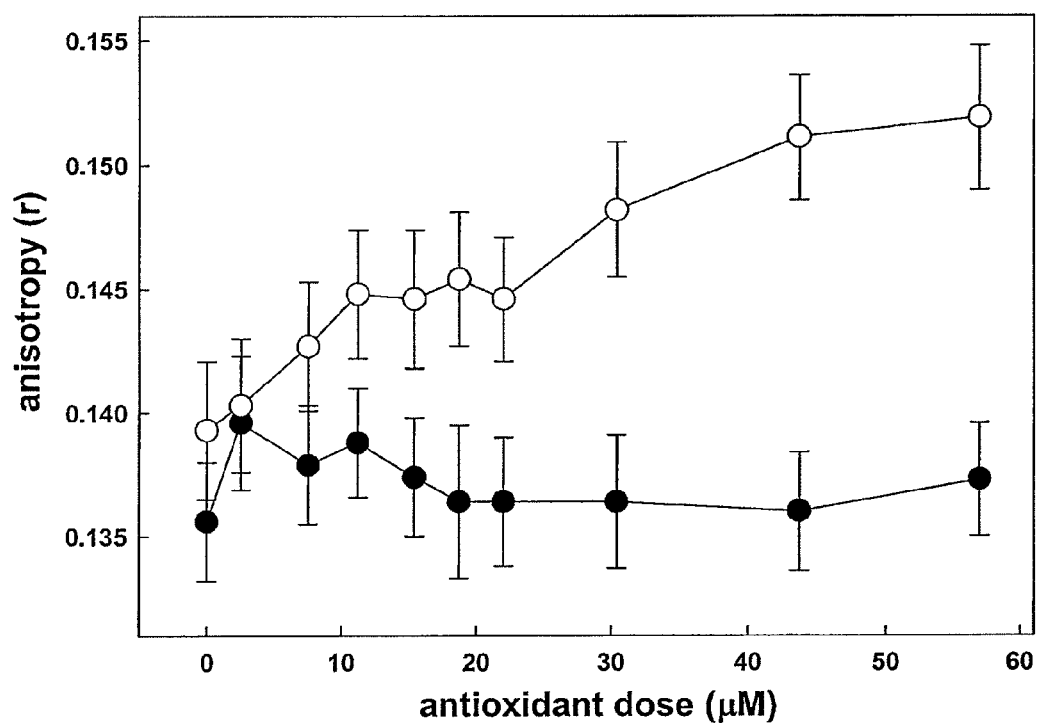
FIG. 7 shows the steady-state anisotropy (r) of DHE fluorescence vs antioxidant dose in DMPC/(21.0 mol %) DHE LUVs at 37° C. LUVs were incubated with increasing doses of either ascorbic acid (closed circles) or ascorbyl palmitate (open circles). Vertical bars are the standard deviations calculated for each experimental run.

Steady-state anisotropy (r) gives information about membrane packing in the vicinity of the probe molecule. A change in the value of r demonstrates a change in membrane free volume. DMPC/DHE LUVs (21.0 mol % DHE) were incubated with increasing doses of either ascorbic acid or ascorbyl palmitate, and steady-state anisotropy measurements were recorded (FIG. 7). The addition of water-soluble ascorbic acid had no effect on the anisotropy value, even at high doses. Ascorbyl palmitate, however, caused a steady increase in r as the dose was increased. Assuming that the fluorescence lifetime of DHE is invariant with antioxidant dose, the anisotropy data (FIG. 7) indicate a decrease in membrane free volume as more ascorbyl palmitate molecules partition into the bilayer. The insertion of the palmitate chain also changes membrane composition, thus altering the actual sterol mole percentage in the membrane and perturbing the dynamic equilibrium of membrane lateral organization. As [ascorbyl palmitate] increases, the lipid bilayer becomes increasingly perturbed, and membrane lateral organization is disrupted. Therefore, the biphasic change in lag phase at $C_r$ is abolished or obliterated above $C_{th}$.

Using the sterol superlattice model as a guide, inventors demonstrate how membrane lateral organization alone directly affects the potency of two common antioxidants. In the case of water-soluble ascorbic acid, it was observed that differences in lateral organization produce a predictable effect on lag phase length. All tested doses of ascorbic acid show that, at maximal sterol superlattice formation, lag phase is shortest and hence sterol is oxidized most rapidly. Since ascorbic acid does not perturb membrane lateral organization via bilayer insertion, we use our results as a basis for comparison to evaluate the profiles generated by incubation with a lipophilic antioxidant.

The ascorbyl palmitate results also demonstrate the importance of membrane organization on antioxidant activity. The biphasic profile produced by incubation with ascorbic acid is also seen at low doses of ascorbyl palmitate ($\leq 15$ μM), but becomes randomized at doses greater than 15 μM. Ascorbyl palmitate readily inserts into the lipid bilayer, as demonstrated by its high log $P_{oct}$ value of 7.19. The log $P_{oct}$ (octanol-water partition coefficient) is the logarithmic ratio of the concentration of a chemical in octanol and in water, and is a measure of the hydrophilicity of a substance (65). At higher doses of ascorbyl palmitate, membrane lateral organization is disrupted and no predictable profile is seen. Our results suggest that the membrane perturbation caused by ascorbyl palmitate may be responsible for some portion of the conflicting clinical results. All of the lipophilic antioxidants administered in large-scale clinical trials were ultimately categorized as "not recommended" due to a lack of substantial evidence demonstrating a benefit. Some trials concluded that lipophilic antioxidants lead to an increased risk for the very conditions they were expected to treat. It is believed that the dose-dependent disruption in membrane lateral organization is at least partially responsible for the deleterious effects seen in some clinical trials. Perhaps lipophilic antioxidants are useful only in small doses, when the degree of membrane perturbation is small. There may be an appropriate threshold dose of a lipophilic antioxidant; for doses below this threshold, the benefits of radical scavenging at the site of the lipid bilayer are conferred, and the use of a lipid-soluble antioxidant is indicated. At doses above this threshold, however, the degree of perturbation of membrane lateral organization leads to deleterious effects on membrane activities, which may override the potential benefits of radical scavenging at the site of the membrane. The threshold value ($C_{th}$) for any given antioxidant can be determined using the strategy illustrated in FIGS. 3-5. One can employ this assay and approach as a first-line screening for new antioxidants and for assessing their possible adverse effects on membranes.

From these three sets of samples examined in this study, it can be concluded that lipid-soluble vitamin C (ascorbyl palmitate) disrupts sterol superlattices relatively easily, with a $C_{th}$ value close to 13.1-15.0 μM. In comparison, the water-soluble counterpart (ascorbic acid) does not seem to be disruptive toward sterol lateral organization in the membrane, even at an antioxidant concentration as high as 120 μM.

This assay allows not only to measure the relative potencies of different antioxidants (on the basis of lag-phase length), but to further characterize an antioxidant based on the degree of membrane disruption it produces. This is an important concept, and may provide insight regarding the use of lipid-soluble antioxidants as prophylactic and therapeutic agents. In many clinical trials, lipophilic antioxidants have not performed as expected, and have failed to protect against free-radical damage. It is possible that before these antioxidants can reliably be recommended, the balance between a long lag phase (induced by increasing doses) and the degree of membrane perturbation on lateral organization (also produced by increasing doses) must be addressed. This information could not only be used to assess the efficacy of known antioxidants, but could allow the modification of these antioxidants or the design of new antioxidants to minimize the adverse effects and optimize the protective properties. For example, it is possible that if the acyl chain of ascorbyl palmitate were shortened, the resulting molecule would cause less membrane perturbation but would still provide longer protection against free radical oxidation than its hydrophilic counterpart, ascorbic acid.

Although this assay was performed on a model membrane system, it could theoretically be extended to lipoprotein particles or cells, provided that the fluorescent cholesterol analogue, DHE, is first incorporated into the membrane or lipid particles. Addition of DHE to a membrane can be accomplished by the use of methyl-β-cyclodextrin (66) or by spontaneous transfer between membranes (67, 68).

In another aspect, the invention is a method of identifying an antioxidant activity of a compound, the method comprising detecting and/or measuring disruption of a sterol superlattice formation, wherein the disruption is caused by oxidation of sterol upon contacting sterol with a prooxidant and the compound.

In another aspect, the invention is a kit for performing an assay for screening and/or ranking antioxidants for strength and toxicity in vitro, the kit comprising: (a) a set of calibrating liposomes where each liposome comprises a fluorescent sterol probe and a phospholipid, wherein a mole fraction of the fluorescent sterol probe is varied from 18 mol % to 52 mole %; (b) an antioxidant; and (c) a prooxidant.

In certain embodiments of the kit, the fluorescent sterol probe is at least one of 5,7,9,(11),22-ergostatetraen-3beta-ol (dehydroergosterol) or 5,7,9,(11)-cholestatrien-3beta-ol or combinations thereof with a non-fluorescent sterol.

In certain embodiments of the kit, the phospholipid is at least one of phosphatidylcholine (PC) or sphingomyelin.

In certain embodiments of the kit, the prooxidant is at least one of 2,2'-azobis(2-methylpropion-amidine)dihydrochloride or 2,2'-azobis(2,4-dimethylvaleronitrile).

In certain embodiments of the kit, the antioxidant is at least one of ascorbyl palmitate, ascorbic acid, or alpha lipoic acid.

The kit can comprise a supporting matrix (e.g., a gel, a plate, etc.), a buffer and any other components suitable for achieving the purposes described above.

The invention will be illustrated in more detail with reference to the following Examples, but it should be understood that the present invention is not deemed to be limited thereto.

Example

Use of Assay on Ascorbic Acid and Ascorbyl Palmitate

The antioxidant-induced lag phase was measured in DMPC/DHE LUVs at 37° C. as a function of sterol mole fraction in samples spanning three critical mole fractions (20.0, 25.0 and 40.0 mol %) (FIGS. 4, 5, and 6). The data presented in FIG. 4 were obtained from the sample set ranging from 18.8-21.2 mol % DHE in DMPC. In this sample set, 20.0 mol % is the only theoretically predicted $C_r$ value. At all the ascorbic acid concentrations tested (5.6-30.0 µM), we detected a biphasic change in lag phase at 19.8±0.21 mol % DHE. Within the experimental errors (69), this sterol mole fraction agrees well with the theoretically predicted $C_r$ value (i.e., 20.0 mol %). This result suggests that ascorbic acid does not disrupt sterol superlattice structures at all doses tested (up to 30 µM in this sample set). In sharp contrast, the biphasic change in lag phase was abolished when the concentration of the lipid soluble vitamin C (ascorbyl palmitate) was increased to 15.0 µM or higher (FIG. 4, right panel). Notice that the single datum point drop at 20.4 mol % at 15.0 µM (FIG. 4, right panel) cannot be counted as a real biphasic change because a genuine biphasic change must have more than one datum point on either side of the biphasic change. These data (FIG. 4, right panel) allow to determine the threshold concentration of ascorbyl palmitate ($C_{th}$), above which a biphasic profile of lag phase at $C_r$ is no longer observable. In this sample set, the $C_{th}$ value for ascorbyl palmitate is between 7.5 and 15.0 µM.

Similar results were obtained for the sample sets ranging from 23.8-26.2 mol % (FIG. 5) and 38.8-41.2 mol % (FIG. 6); in these two regions, the only theoretical $C_r$ values are 25.0 and 40.0 mol % sterol, respectively. A biphasic change in lag phase at 25.0 mol % and 40.0 mol % remain clearly observable even at the highest ascorbic acid concentration examined (30 µM for the sample set shown in FIG. 5 or 120 µM for the set shown in FIG. 6). However, for the lipid-soluble antioxidant ascorbyl palmitate, the biphasic change in lag phase with sterol content is abolished at $C_{th}$=11.3-15.0 µM for data shown in FIG. 5 and 13.1-15.0 µM for the data shown in FIG. 6.

To demonstrate that ascorbyl palmitate can cause membrane disruption whereas ascorbic acid does not, the steady-state anisotropy of DHE fluorescence in 21.0 mol % DHE/DMPC LUVs was measured as a function of increasing antioxidant dose (FIG. 7). DHE fluorescence anisotropy is almost invariant with ascorbic acid dose, but undergoes a significant increase with increasing ascorbyl palmitate concentration (FIG. 7).

The data show that ascorbyl palmitate has a $C_{th}$ value of ~13-15 µM while ascorbic acid has a $C_{th}$ value>>120 µM.

While the invention has been described in detail and with reference to specific examples thereof, it will be apparent to one skilled in the art that various changes and modifications can be made therein without departing from the spirit and scope thereof.

REFERENCES

1. Collin, B., Busseuil, D., Zeller, M., Perrin, C., Barthez, O., Duvillard, L., Vergely, C., Bardou, M., Dumas, M., Cottin, Y., and Rochette, L. (2007) Increased Superoxide Anion Production is Associated with Early Atherosclerosis and Cardiovascular Dysfunctions in a Rabbit Model. Mol. Cell. Biochem. 294, 225-235.
2. Pelicano, H., Carney, D., and Huang, P. (2004) ROS Stress in Cancer Cells and Therapeutic Implications. Drug Resist Updat. 7, 97-110.
3. Stocker, R., and Keaney, J. F., Jr. (2004) Role of Oxidative Modifications in Atherosclerosis. Physiol. Rev. 84, 1381-1478.
4. Brown, N. S., and Bicknell, R. (2001) Hypoxia and Oxidative Stress in Breast Cancer. Oxidative Stress Its Effects on the Growth, Metastatic Potential and Response to Therapy of Breast Cancer. Breast Cancer Res. 3, 323-327.
5. Panini, S. R., and Sinensky, M. S. (2001) Mechanisms of Oxysterol-Induced Apoptosis. Curr. Opin. Lipidol. 12, 529-533.
6. Moslen, M. T. (1994) Free Radicals in Diagnostic Medicine. Plenum Press, New York.
7. Ames, B. N., Shigenaga, M. K., and Hagen, T. M. (1993) Oxidants, Antioxidants, and the Degenerative Diseases of Aging. Proc. Natl. Acad. Sci. U.S.A. 90, 7915-7922.
8. Stampfer, M. J., Hennekens, C. H., Manson, J. E., Colditz, G. A., Rosner, B., and Willett, W. C. (1993) Vitamin E Consumption and the Risk of Coronary Disease in Women. N. Engl. J. Med. 328, 1444-1449.
9. Rimm, E. B., Stampfer, M. J., Ascherio, A., Giovannucci, E., Colditz, G. A., and Willett, W. C. (1993) Vitamin E Consumption and the Risk of Coronary Heart Disease in Men. N. Engl. J. Med. 328, 1450-1456.
10. Sigounas, G., Anagnostou, A., and Steiner, M. (1997) Dl-Alpha-Tocopherol Induces Apoptosis in Erythroleukemia, Prostate, and Breast Cancer Cells. Nutr. Cancer. 28, 30-35.
11. Zhang, Y., Ni, J., Messing, E. M., Chang, E., Yang, C. R., and Yeh, S. (2002) Vitamin E Succinate Inhibits the Function of Androgen Receptor and the Expression of Prostate-Specific Antigen in Prostate Cancer Cells. Proc. Natl. Acad. Sci. U.S.A. 99, 7408-7413.
12. Zu, K., and Ip, C. (2003) Synergy between Selenium and Vitamin E in Apoptosis Induction is Associated with Activation of Distinctive Initiator Caspases in Human Prostate Cancer Cells. Cancer Res. 63, 6988-6995.
13. Lonn, E., Bosch, J., Yusuf, S., Sheridan, P., Pogue, J., Arnold, J. M., Ross, C., Arnold, A., Sleight, P., Probstfield, J., Dagenais, G. R., and HOPE and HOPE-TOO Trial Investigators. (2005) Effects of Long-Term Vitamin E Supplementation on Cardiovascular Events and Cancer: A Randomized Controlled Trial. JAMA. 293, 1338-1347.
14. Uneri, C., Sari, M., Baglam, T., Polat, S., and Yuksel, M. (2006) Effects of Vitamin E on Cigarette Smoke Induced Oxidative Damage in Larynx and Lung. Laryngoscope. 116, 97-100.
15. Miller, E. R., 3rd, Pastor-Barriuso, R., Dalal, D., Riemersma, R. A., Appel, L. J., and Guallar, E. (2005) Meta-Analysis: High-Dosage Vitamin E Supplementation may Increase all-Cause Mortality. Ann. Intern. Med. 142, 37-46.
16. Waters, D. D., Alderman, E. L., Hsia, J., Howard, B. V., Cobb, F. R., Rogers, W. J., Ouyang, P., Thompson, P., Tardif, J. C., Higginson, L., Bittner, V., Steffes, M., Gordon, D. J., Proschan, M., Younes, N., and Verter, J. I. (2002) Effects of Hormone Replacement Therapy and Antioxidant Vitamin Supplements on Coronary Atherosclerosis in Postmenopausal Women: A Randomized Controlled Trial. JAMA. 288, 2432-2440.
17. Pham, D. Q., and Plakogiannis, R. (2005) Vitamin E Supplementation in Cardiovascular Disease and Cancer Prevention: Part 1. Ann. Pharmacother. 39, 1870-1878.
18. Gaziano, J. M., Manson, J. E., Branch, L. G., Colditz, G. A., Willett, W. C., and Buring, J. E. (1995) A Prospective Study of Consumption of Carotenoids in Fruits and Vegetables and Decreased Cardiovascular Mortality in the Elderly. Ann. Epidemiol. 5, 255-260.
19. Osganian, S. K., Stampfer, M. J., Rimm, E., Spiegelman, D., Manson, J. E., and Willett, W. C. (2003) Dietary Carotenoids and Risk of Coronary Artery Disease in Women. Am. J. Clin. Nutr. 77, 1390-1399.
20. Tung, K. H., Wilkens, L. R., Wu, A. H., McDuffie, K., Hankin, J. H., Nomura, A. M., Kolonel, L. N., and Goodman, M. T. (2005) Association of Dietary Vitamin A, Carotenoids, and Other Antioxidants with the Risk of Ovarian Cancer. Cancer Epidemiol. Biomarkers Prev. 14, 669-676.
21. Briviba, K., Schnabele, K., Schwertle, E., Blockhaus, M., and Rechkemmer, G. (2001) Beta-Carotene Inhibits Growth of Human Colon Carcinoma Cells in Vitro by Induction of Apoptosis. Biol. Chem. 382, 1663-1668.
22. Modnicki, D., and Matlawska, I. (2005) Carotenoids as Components of Dietary Supplements Recommended for Smokers and Persons Passively Exposed to Cigarette Smoke. Przegl. Lek. 62, 1188-1189.
23. Sesso, H. D. (2006) Carotenoids and Cardiovascular Disease: What Research Gaps Remain? Curr. Opin. Lipidol. 17, 11-16.
24. Pokorski, M., and Marczak, M. (2005) Stability of Ascorbyl Palmitate Molecule in the Rat Brain. J. Physiol. Pharmacol. 56 Suppl 4, 197-201.
25. Pokorski, M., Marczak, M., Dymecka, A., and Suchocki, P. (2003) Ascorbyl Palmitate as a Carrier of Ascorbate into Neural Tissues. J. Biomed. Sci. 10, 193-198.
26. Smart, R. C., and Crawford, C. L. (1991) Effect of Ascorbic Acid and its Synthetic Lipophilic Derivative Ascorbyl Palmitate on Phorbol Ester-Induced Skin-Tumor Promotion in Mice. Am. J. Clin. Nutr. 54, 1266S-1273S.
27. Ross, D., Mendiratta, S., Qu, Z. C., Cobb, C. E., and May, J. M. (1999) Ascorbate 6-Palmitate Protects Human Erythrocytes from Oxidative Damage. Free Radic. Biol. Med. 26, 81-89.
28. Jonker, D., Lee, V. S., Hargreaves, R. J., and Lake, B. G. (1988) Comparison of the Effects of Ascorbyl Palmitate and L-Ascorbic Acid on Paracetamol-Induced Hepatotoxicity in the Mouse. Toxicology. 52, 287-295.
29. Smart, R. C., Huang, M. T., Han, Z. T., Kaplan, M. C., Focella, A., and Conney, A. H. (1987) Inhibition of 12-O-Tetradecanoylphorbol-13-Acetate Induction of Ornithine Decarboxylase Activity, DNA Synthesis, and Tumor Promotion in Mouse Skin by Ascorbic Acid and Ascorbyl Palmitate. Cancer Res. 47, 6633-6638.
30. Perricone, N. V., Nagy, K., Horvath, F., Dajko, G., Uray, I., and Zs-Nagy, I. (1999) The Hydroxyl Free Radical Reactions of Ascorbyl Palmitate as Measured in various in Vitro Models. Biochem. Biophys. Res. Commun. 262, 661-665.
31. Meves, A., Stock, S, N., Beyerle, A., Pittelkow, M. R., and Peus, D. (2002) Vitamin C Derivative Ascorbyl Palmitate Promotes Ultraviolet-B-Induced Lipid Peroxidation and Cytotoxicity in Keratinocytes. J. Invest. Dermatol. 119, 1103-1108.
32. Kaap, S., Brechlin, P., Quentin, I., Eger, K., and Steinfelder, H. J. (2004) Apoptosis by 6-O-Palmitoyl-L-Ascorbic Acid Coincides with JNK-Phosphorylation and Inhibition of Mg2+-Dependent Phosphatase Activity. Biochem. Pharmacol. 67, 919-926.
33. Pinnell, S. R. (2002) Ascorbyl-6-Palmitate is Not Ascorbic Acid. J. Invest. Dermatol. 119, 991.
34. Heinecke, J. W. (2001) Is the Emperor Wearing Clothes? Clinical Trials of Vitamin E and the LDL Oxidation Hypothesis. Arterioscler. Thromb. Vasc. Biol. 21, 1261-1264.
35. Siems, W., Sommerburg, O., Schild, L., Augustin, W., Langhans, C. D., and Wiswedel, I. (2002) Beta-Carotene Cleavage Products Induce Oxidative Stress in Vitro by Impairing Mitochondrial Respiration. FASEB J. 16, 1289-1291.
36. Atkin, M. A., Gasper, A., Ullegaddi, R., and Powers, H. J. (2005) Oxidative Susceptibility of Unfractionated Serum Or Plasma: Response to Antioxidants in Vitro and to Antioxidant Supplementation. Clin. Chem. 51, 2138-2144.
37. Rietveld, A., and Wiseman, S. (2003) Antioxidant Effects of Tea: Evidence from Human Clinical Trials. J. Nutr. 133, 3285S-3292S.
38: Simon Y. L. Ching, Jon Hall, Kevin Croft, John Beilby, Enrico Rossi and Emilio Ghisalberti (2006) Antioxidant Inhibition of Oxygen Radicals for Measurement of Total Antioxidant Capacity in Biological Samples. Analytical Biochemistry, 353, 257-265.
39. Naguib, Y. M. A. (2000) A Fluorometric Method for Measurement of Oxygen Radical-Scavenging Activity of Water-Soluble Antioxidants. Analytical Biochemistry, 284, 93-98.
40. Huang, D., Ou, B., and Prior, R. L. (2005) The Chemistry Behind Antioxidant Capacity Assays. J. Agric. Food Chem. 53, 1841-1856.
41. Schlesier, K., Harwat, M., Bohm, V., and Bitsch, R. (2002) Assessment of Antioxidant Activity by using Different in Vitro Methods. Free Radic. Res. 36, 177-187.
42. Young, I. S. (2001) Measurement of Total Antioxidant Capacity. J. Clin. Pathol. 54, 339.
43. Olsher, M., Yoon, S. I., and Chong, P. L.-G. (2005) Role of Sterol Superlattice in Free Radical-Induced Sterol Oxidation in Lipid Membranes. Biochemistry. 44, 2080-2087.
44. Schroeder, F., Jefferson, J. R., Kier, A. B., Knittel, J., Scallen, T. J., Wood, W. G., and Hapala, I. (1991) Membrane Cholesterol Dynamics: Cholesterol Domains and Kinetic Pools. Proc. Soc. Exp. Biol. Med. 196, 235-252.
45. Chong, P. L.-G. (1994) Evidence for Regular Distribution of Sterols in Liquid Crystalline Phosphatidylcholine Bilayers. Proc. Natl. Acad. Sci. 91, 10069-10073.
46. Virtanen, J. A., Ruonala, M., Vauhkonen, M., and Somerharju, P. (1995) Lateral Organization of Liquid-Crystalline Cholesterol-Dimyristoylphosphatidylcholine Bilayers. Evidence for Domains with Hexagonal and Centered Rectangular Cholesterol Superlattices. Biochemistry. 34, 11568-11581.
47. Chong, P. L.-G., and Sugar, I. P. (2002) Fluorescence Studies of Lipid Regular Distribution in Membranes. Chem. Phys. Lipids. 116, 153-175.
48. Chong, P. L.-G., and Olsher, M. (2004) Fluorescence Studies of the Existence and Functional Importance of Regular Distributions in Liposomal Membranes. Soft Materials. 2, 85-108.
49. Somerharju, P., Virtanen, J. A., and Cheng, K. H. (1999) Lateral Organisation of Membrane Lipids. the Superlattice View. Biochim. Biophys. Acta. 1440, 32-48.
50. Venegas, B., Sugar, I. P., and Chong, P. L.-. (2007) Critical Factors for Detection of Biphasic Changes in Membrane Properties at Specific Sterol Mole Fractions for Maximal Superlattice Formation. J. Phys. Chem. B. 111, 5180-5192.
51. Wang, M. M., Sugar, I. P., and Chong, P. L.-G. (1998) Role of the Sterol Superlattice in the Partitioning of the Antifungal Drug Nystatin into Lipid Membranes. Biochemistry. 37, 11797-11805.
52. Liu, F., and Chong, P. L.-G. (1999) Evidence for a Regulatory Role of Cholesterol Superlattices in the Hydrolytic Activity of Secretory Phospholipase A2 in Lipid Membranes. Biochemistry. 38, 3867-3873.
53. Wang, M. M., Olsher, M., Sugar, I. P., and Chong, P. L.-G. (2004) Cholesterol Superlattice Modulates the Activity of Cholesterol Oxidase in Lipid Membranes. Biochemistry. 43, 2159-2166.
54. Olsher, M., Yoon, S. I., and Chong, P. L.-G. (2005) Role of Sterol Superlattice in Free Radical-Induced Sterol Oxidation in Lipid Membranes. Biochemistry. 44, 2080-2087.
55. Cannon, B., Hermanssoni, M., Gyorke, S., Somerharju, P., Virtanen, J. A., and Cheng, K. H. (2003) Regulation of 56. Cuevas, F. J., Jameson, D. M., and Sotomayor, C. P. (2006) Modulation of Reconstituted Pig Kidney Na+/K+-ATPase Activity by Cholesterol in Endogenous Lipid Vesicles: Role of Lipid Domains. Biochemistry. 45, 13855-13868.
57. Diaz, M. N., Frei, B., Vita, J. A., and Keaney, J. F., Jr. (1997) Antioxidants and Atherosclerotic Heart Disease. N. Engl. J. Med. 337, 408-416.
58. Chang, J., and Phelan, K. (2002) The Effects of Oxysterols on Cells of the Nervous System, in Sterols and Oxysterols: Chemistry, Biology, and Pathobiology 2002 (S. J. Fliesler, Ed.) Research Signpost, USA.
59. van Reyk, D. M., and Jessup, W. (1999) The Macrophage in Atherosclerosis: Modulation of Cell Function by Sterols. J. Leukoc. Biol. 66, 557-561.
60. Brown, D. A., and London, E. (1998) Functions of Lipid Rafts in Biological Membranes. Annu. Rev. Cell Dev. Biol. 14, 111-136.
61. Bartlett, G. R. (1959) Phosphorus Assay in Column Chromatography. J. Biol. Chem. 234, 466-468.
62. Chong, P. L.-G., Liu, F., Wang, M. M., Truong, K., Sugar, I. P., and Brown, R. E. (1996) Fluorescence Evidence for Cholesterol Regular Distribution in Phosphatidylcholine and in Sphingomyelin Lipid Bilayers. J. Fluorescence. 6, 221-230.
63. Simons, K., and Ikonen, E. (1997) Functional Rafts in Cell Membranes. Nature. 387, 569-572.
64. Kusumi, A., Koyama-Honda, I., and Suzuki, K. (2004) Molecular Dynamics and Interactions for Creation of Stimulation-Induced Stabilized Rafts from Small Unstable Steady-State Rafts. Traffic. 5, 213-230.
65. Uner, M., Wissing, S. A., Yener, G., and Muller, R. H. (2005) Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel. Pharmazie. 60, 751-755.
66. Rothblat, G. H., and Phillips, M. C. (1982) Mechanism of Cholesterol Efflux from Cells. Effects of Acceptor Structure and Concentration. J. Biol. Chem. 257, 4775.
67. Bar, L. K., Chong, P. L.-G., Barenholz, Y., and Thompson, T. E. (1989) Spontaneous Transfer between Phospholipid Bilayers of Dehydroergosterol, a Fluorescent Cholesterol Analog. Biochim. Biophys. Acta. 983, 109-112.
68. Broadley, C., Dawidowicz, E. A., Chong, P. L.-G., and Hoover, R. (1991) Modulation of Membrane Cholesterol Levels: Effects on Endothelial Cell Function. Exp. Cell Res. 193, 144-150.
69. Liu, F., Sugar, I. P., and Chong, P. L.-G. (1997) Cholesterol and Ergosterol Superlattices in Three-Component Liquid Crystalline Lipid Bilayers as Revealed by Dehydroergosterol Fluorescence. Biophys. J. 72, 2243-2254.

What is claimed is:

1. A method of screening an antioxidant for potential toxicity in vitro, the method comprising:
   (a) providing a constant absolute amount of a fluorescent sterol probe having a detectable signal, a bilayer forming lipid and optionally a spacing lipid to form a model system comprising unilamellar vesicles having a sterol superlattice formation, wherein a mole fraction of a sterol, including the fluorescent sterol probe, is varied from 18 mol % to 52 mole % in increments of about 0.3 mol %;
   (b) providing an antioxidant;
   (c) providing a prooxidant;
   (d) combining the unilamellar vesicles, the antioxidant and the prooxidant;
   (e) measuring (1) a fluorescence intensity of the fluorescent sterol probe from a time of the addition of the prooxidant to at least 5 minutes after a time of an abrupt change in sterol oxidation rate, and thereby obtaining a lag phase length ($\tau$), or (2) a sterol fluorescence intensity from a time of the addition of the prooxidant to a time when the sterol fluorescence intensity vs. time begins to deviate from linearity, and thereby obtaining an initial rate of sterol oxidation in the presence of the antioxidant (Ri) and an initial rate of sterol oxidation in the absence of the antioxidant (Rio);
   (f) plotting the $\tau$, or the Ri as a function of the sterol mole fraction to detect a biphasic effect; and
   (g) repeating said measuring at increasing doses of the antioxidant to determine a threshold concentration ($C_{th}$) of the antioxidant at which the biphasic effect substantially disappears,
   wherein a lower $C_{th}$ indicates a higher potential toxicity of the antioxidant.

2. The method of claim 1, wherein the fluorescent sterol probe is at least one of 5,7,9,(11),22-ergostatetraen-3beta-ol, 5,7,9,(11)-cholestatrien-3beta-ol, or combinations thereof with a non-fluorescent sterol.

3. The method of claim 2, wherein the non-fluorescent sterol is at least one of cholesterol, or ergosterol.

4. The method of claim 1, wherein the bilayer forming lipid is at least one of phosphatidylcholine (PC) or sphingomyelin.

5. The method of claim 1, wherein the prooxidant is at least one of 2,2'-azobis(2-methylpropion-amidine) dihydrochloride or 2,2'-azobis(2,4-dimethylvaleronitrile).

6. The method of claim 1, wherein the antioxidant is at least one of ascorbyl palmitate, ascorbic acid, or alpha lipoic acid.

7. The method of claim 1, wherein said measuring is conducted in the presence of a buffer.

8. A kit for screening using the method of claim 1, the kit comprising:
   a) a set of calibrating liposomes where each liposome comprises a fluorescent sterol probe and a phospholipid, wherein an absolute amount of the fluorescent sterol probe remains constant and a mole fraction of the fluorescent sterol probe is varied from 18 mol % to 52 mole % in increments of about 0.3 mol %;
   b) an antioxidant; and
   c) a prooxidant.

9. The kit of claim 8, wherein the fluorescent sterol probe is at least one of 5,7,9,(11),22-ergostatetraen-3beta-ol, 5,7,9,(11)-cholestatrien-3beta-ol, or combinations thereof with a non-fluorescent sterol.

10. The kit of claim 8, wherein the phospholipid is at least one of phosphatidylcholine (PC) or sphingomyelin.

11. The kit of claim 8, wherein the prooxidant is at least one of 2,2'-azobis(2-methylpropion-amidine) dihydrochloride or 2,2'-azobis(2,4-dimethylvaleronitrile).

12. The kit of claim 8, wherein the antioxidant is at least one of ascorbyl palmitate, ascorbic acid, or alpha lipoic acid.

13. The kit of claim 8, further comprising a buffer.

14. The kit of claim 8, further comprising a supporting matrix.

15. A method of screening an antioxidant for potency and/or potential toxicity in vitro, the method comprising measuring disruption of a membrane comprising a sterol superlattice formation upon contact with an antioxidant, wherein the disruption is caused by an insertion of the antioxidant into the membrane; and determining a threshold antioxidant concentration ($C_{th}$) at which the antioxidant begins to disrupt the sterol superlattice formation, wherein a lower $C_{th}$ indicates a higher potential toxicity of the antioxidant.

16. A method of screening an antioxidant for potency in vitro, the method comprising:
(a) providing a constant absolute amount of a fluorescent sterol probe having a detectable signal, a bilayer forming lipid and optionally a spacing lipid to form a model system comprising unilamellar vesicles having a sterol superlattice formation, wherein a mole fraction of sterol, including the fluorescent sterol probe, is varied from 18 mol % to 52 mole % in increments of about 0.3 mol %;
(b) providing an antioxidant;
(c) providing a prooxidant;
(d) combining the unilamellar vesicles, the antioxidant and the prooxidant;
(e) measuring a sterol fluorescence intensity from a time of the addition of the prooxidant to a time when the sterol fluorescence intensity vs. time begins to deviate from linearity, and thereby obtaining an initial rate of sterol oxidation in the presence of the antioxidant (Ri) and an initial rate of sterol oxidation in the absence of the antioxidant (Rio), wherein no lag phase length is obtained when the fluorescence intensity of the fluorescent sterol probe is measured from a time of the addition of the prooxidant to at least 5 minutes after a time of an abrupt change in sterol oxidation rate; and
(f) determining an Ri/Rio, wherein a lower Ri/Rio indicates a higher potency of the antioxidant.

* * * * *